(12) United States Patent
Chang et al.

(10) Patent No.: US 9,494,500 B2
(45) Date of Patent: Nov. 15, 2016

(54) COLLECTION AND CONCENTRATION SYSTEM FOR BIOLOGIC SUBSTANCE OF INTEREST AND USE THEREOF

(71) Applicant: Academia Sinica, Taipei (TW)

(72) Inventors: Ying-Chih Chang, Taipei (TW); Chia-Hsien Hsu, Zhunan Town (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/065,265

(22) Filed: Oct. 28, 2013

(65) Prior Publication Data

US 2014/0120537 A1  May 1, 2014

Related U.S. Application Data

(60) Provisional application No. 61/719,491, filed on Oct. 29, 2012.

(51) Int. Cl.
| | | |
|---|---|---|
| C12M 1/00 | (2006.01) | |
| G01N 1/40 | (2006.01) | |
| B01L 3/00 | (2006.01) | |
| B01D 61/18 | (2006.01) | |
| B01D 63/08 | (2006.01) | |

(52) U.S. Cl.
CPC ......... *G01N 1/405* (2013.01); *B01L 3/502715* (2013.01); *B01L 3/502753* (2013.01); *B01D 61/18* (2013.01); *B01D 63/088* (2013.01); *B01L 2200/027* (2013.01); *B01L 2300/0681* (2013.01); *B01L 2300/163* (2013.01)

(58) Field of Classification Search
CPC .......................... G01N 1/405; B01L 3/502715

USPC ............................... 435/283.1; 422/502, 527
See application file for complete search history.

(56) References Cited

U.S. PATENT DOCUMENTS

| | | | |
|---|---|---|---|
| 5,707,799 A | 1/1998 | Hansmann et al. | |
| 5,837,115 A | 11/1998 | Austin et al. | |
| 5,842,787 A | 12/1998 | Kopf-Sill et al. | |
| 5,952,173 A | 9/1999 | Hansmann et al. | |

(Continued)

FOREIGN PATENT DOCUMENTS

| | | |
|---|---|---|
| CN | 1646912 A | 7/2005 |
| CN | 102011193 A | 4/2011 |

(Continued)

OTHER PUBLICATIONS

Adams, et al. Integrated acoustic and magnetic separation in microfluidic channels. Appl Phys Lett. Dec. 21, 2009;95(25):254103.

(Continued)

*Primary Examiner* — Betty Forman
(74) *Attorney, Agent, or Firm* — Wilson Sonsini Goodrich & Rosati

(57) ABSTRACT

A system and method thereof for collecting and concentrating a biologic substance of interest is provided. The biologic of interest obtained from a biologic sample present at an initial low concentration (or low number counts) can be captured and released through a collection device of the system to an intermediate second concentration, and further recovered through a concentration device of the system to a third concentration, thereby facilitating subsequent detection, characterization, enumeration, immunostaining, inspection, imaging, culturing, molecular analysis, and/or other assays.

21 Claims, 8 Drawing Sheets

(56) References Cited

U.S. PATENT DOCUMENTS

| | | | |
|---|---|---|---|
| 6,562,616 B1 | 5/2003 | Toner et al. | |
| 6,632,652 B1 | 10/2003 | Austin et al. | |
| 6,676,904 B1* | 1/2004 | Lee et al. | 422/535 |
| 6,685,841 B2 | 2/2004 | Lopez et al. | |
| 6,955,738 B2 | 10/2005 | Derand et al. | |
| 7,150,812 B2 | 12/2006 | Huang et al. | |
| 7,276,170 B2 | 10/2007 | Oakey et al. | |
| 7,318,902 B2 | 1/2008 | Oakey et al. | |
| 7,472,794 B2 | 1/2009 | Oakey et al. | |
| 7,735,652 B2 | 6/2010 | Inglis et al. | |
| 7,799,567 B1* | 9/2010 | Call | 436/53 |
| 7,988,840 B2 | 8/2011 | Huang et al. | |
| 7,993,821 B2 | 8/2011 | Chiu et al. | |
| 8,021,614 B2 | 9/2011 | Huang et al. | |
| 8,025,854 B2 | 9/2011 | Ohman et al. | |
| D650,091 S | 12/2011 | Odeh | |
| 8,282,799 B2 | 10/2012 | Huang et al. | |
| 8,304,230 B2 | 11/2012 | Toner et al. | |
| 8,343,440 B2 | 1/2013 | Yoshioka | |
| 8,372,579 B2 | 2/2013 | Toner et al. | |
| 8,579,117 B2 | 11/2013 | Loutherback et al. | |
| 8,669,044 B2 | 3/2014 | Chiu et al. | |
| 8,895,298 B2 | 11/2014 | Toner et al. | |
| 8,986,966 B2 | 3/2015 | Toner et al. | |
| 8,986,988 B2 | 3/2015 | Karnik et al. | |
| 9,016,221 B2 | 4/2015 | Brennan et al. | |
| 9,056,318 B2 | 6/2015 | Bergman et al. | |
| 9,174,222 B2 | 11/2015 | Huang et al. | |
| 2002/0055093 A1* | 5/2002 | Abbott | G01N 33/54353 435/5 |
| 2003/0157054 A1 | 8/2003 | Gillies et al. | |
| 2004/0245102 A1* | 12/2004 | Gilbert et al. | 204/451 |
| 2005/0230272 A1 | 10/2005 | Lee et al. | |
| 2006/0002825 A1 | 1/2006 | Derand et al. | |
| 2006/0237390 A1 | 10/2006 | King et al. | |
| 2007/0026381 A1 | 2/2007 | Huang et al. | |
| 2007/0026416 A1 | 2/2007 | Fuchs | |
| 2007/0059716 A1 | 3/2007 | Balis et al. | |
| 2007/0202536 A1* | 8/2007 | Yamanishi | C12Q 1/6881 435/7.1 |
| 2007/0231851 A1 | 10/2007 | Toner et al. | |
| 2008/0090239 A1* | 4/2008 | Shoemaker | G01N 33/5091 435/6.12 |
| 2009/0036982 A1 | 2/2009 | Aharoni et al. | |
| 2009/0136982 A1* | 5/2009 | Tang | B01F 5/102 435/29 |
| 2009/0203536 A1 | 8/2009 | Vermette et al. | |
| 2010/0055733 A1 | 3/2010 | Lutolf et al. | |
| 2010/0092491 A1 | 4/2010 | Anastasi et al. | |
| 2010/0112026 A1 | 5/2010 | Karp et al. | |
| 2010/0151491 A1 | 6/2010 | Himmelhaus et al. | |
| 2010/0233694 A1* | 9/2010 | Kopf-Sill | G01N 33/5091 435/6.14 |
| 2011/0091864 A1* | 4/2011 | Karlsson et al. | 435/4 |
| 2011/0171663 A1 | 7/2011 | Smith et al. | |
| 2011/0250679 A1 | 10/2011 | Chang | |
| 2011/0294186 A1 | 12/2011 | Fuchs et al. | |
| 2012/0015835 A1 | 1/2012 | Fuchs et al. | |
| 2012/0058302 A1 | 3/2012 | Eggenspieler et al. | |
| 2012/0058500 A1 | 3/2012 | Mitchell et al. | |
| 2014/0255976 A1 | 9/2014 | Chang et al. | |
| 2016/0059234 A1 | 3/2016 | Chang et al. | |

FOREIGN PATENT DOCUMENTS

| | | |
|---|---|---|
| EP | 2359689 A1 | 8/2011 |
| EP | 1569510 B1 | 11/2011 |
| GB | 2472927 B | 5/2011 |
| WO | WO-2007048459 A1 | 5/2007 |
| WO | WO 2007/079229 A2 | 7/2007 |
| WO | WO 2007/079250 A2 | 7/2007 |
| WO | WO 2009/140326 A2 | 11/2009 |
| WO | WO 2010/124227 A2 | 10/2010 |
| WO | WO-2010123608 A2 | 10/2010 |
| WO | WO-2010132795 A2 | 11/2010 |
| WO | WO 2012/016136 A2 | 2/2012 |
| WO | WO 2012/094642 A2 | 7/2012 |
| WO | WO-2013003624 A2 | 1/2013 |

OTHER PUBLICATIONS

Bhagat, et al. Continuous particle separation in spiral microchannels using Dean flows and differential migration. Lab Chip. Nov. 2008;8(11):1906-14. doi: 10.1039/b807107a. Epub Sep. 24, 2008.

Cima, et al. Label-free isolation of circulating tumor cells in microfluidic devices: Current research and perspectives. Biomicrofluidics. Jan. 24, 2013;7(1):11810. doi: 10.1063/1.4780062. eCollection 2013.

Dainiak, et al. Cell chromatography: separation of different microbial cells using IMAC supermacroporous monolithic columns. Biotechnol Prog. Mar.-Apr. 2005;21(2):644-9.

Dickson, et al. Efficient capture of circulating tumor cells with a novel immunocytochemical microfluidic device. Biomicrofluidics. Sep. 2011;5(3):34119-3411915. doi: 10.1063/1.3623748. Epub Aug. 22, 2011.

European search report and written opinion dated May 2, 2015 for EP Application No. 12805303.0.

Gervais, Luc. Capillary Microfluidic Chips for Point-of-Care Testing: from Research Tools to Decentralized Medical Diagnostics. InfoScience. 2011. Thesis 5047. Available at http://infoscience.epfl.ch/record/165376/files/EPFL_TH5047.pdf.

Hsiung, et al. A planar interdigitated ring electrode array via dielectrophoresis for uniform patterning of cells. Biosens Bioelectron. Dec. 1, 2008;24(4):869-875.

Hsu, et al. Microvortex for focusing, guiding and sorting of particles. Lab Chip. Dec. 2008;8(12):2128-34. doi: 10.1039/b813434k. Epub Oct. 30, 2008.

Karabacak, et al. Microfluidic, marker-free isolation of circulating tumor cells from blood samples. Nat Protoc. Mar. 2014;9(3):694-710. doi: 10.1038/nprot.2014.044. Epub Feb. 27, 2014.

Nagrath, et al. Isolation of rare circulating tumour cells in cancer patients by microchip technology. Nature. Dec. 20, 2007;450(7173):1235-9.

Ozkumur, et al. Inertial focusing for tumor antigen-dependent and -independent sorting of rare circulating tumor cells. Sci Transl Med. Apr. 3, 2013;5(179):179ra47. doi: 10.1126/scitranslmed.3005616.

Stott, et al. Isolation of circulating tumor cells using a microvortex-generating herringbone-chip. Proc Natl Acad Sci U S A. Oct. 26, 2010;107(43):18392-7. doi: 10.1073/pnas.1012539107. Epub Oct. 7, 2010.

Stroock, et al. Chaotic mixer for microchannels. Science. Jan. 25, 2002;295(5555):647-51.

Tan, et al. Versatile label free biochip for the detection of circulating tumor cells from peripheral blood in cancer patients. Biosens Bioelectron. Dec. 15, 2010;26(4):1701-5. doi: 10.1016/j.bios.2010.07.054. Epub Jul. 22, 2010.

U.S. Appl. No. 14/836,390, filed Aug. 26, 2015, Chang et al.

U.S. Appl. No. 14/781,165, filed Sep. 29, 2015, Chang et al.

Ananthanarayanan, et al. Neural stem cell adhesion and proliferation on phospholipid bilayers functionalized with RGD peptides. Biomaterials, Elsevier Science Publishers BV., Barking GB, vol. 31, No. 33, Nov. 1, 2010, pp. 8706-8715.

"European search report dated Jan. 29, 2016 for EP 15182577.5".

Huang, et al. Type I Collagen-Functionalized Supported Lipid Bilayer as a Cell Culture Platform. Biomacromolecules, vol. 11, No. 5, May 10, 2010, pp. 1231-1240.

Kaladhar, et al. Cell mimetic lateral stabilization of outer cell mimetic bilayer on polymer surfaces by peptide bonding and their blood compatibility. J Biomed Mater Res A. Oct. 2006;79(1):23-35.

Lin, et al. Adhesion of antibody-functionalized polymersomes. Langmuir. Apr. 25, 2006;22(9):3975-9.

Lin, J.J. et al. 2006. Adhesion of antibody-functionalized polymersomes. Langmuir 22: 3975-3979. specif. pp. 3975, 3979.

Office action dated Mar. 23, 2016 for U.S. Appl. No. 14/128,354.

"Office action dated Mar. 23, 2016 for U.S. Appl. No. 14128345".

(56) References Cited

OTHER PUBLICATIONS

"Office action dated Mar. 9, 2016 for U.S. Appl. No. 14065265".
Phillips, et al. Enrichment of cancer cells using aptamers immobilized on a microfluidic channel. Anal Chem. Feb. 1, 2009;81(3):1033-9. doi: 10.1021/ac802092j.
Phillips, J.A. et al. 2009. Enrichment of cancer cells using aptamers immobilized on a microfluidic channel. Analytical Chemistry81 : 1 033-1 039. specif. pp. 1 034, 1 035, 1 036, 1 037, 1 038.
Xu, et al. Aptamer-based microfluidic device for enrichment, sorting, and detection of multiple cancer cells. Anal Chem. Sep. 1, 2009;81(17):7436-42. doi: 10.1021/ac9012072.
Xu, Y. et al. 2009. Aptamer-based microfluidic device for enrichment, sorting, and detection of multiple cancer cells. AnalyticalChemistry 81: 7436-7442. specif. pp. 7436, 7437, 7439, 7440.
Lawrence, et al. Leukocytes roll on a selectin at physiologic flow rates: distinction from and prerequisite for adhesion through integrins.Cell. May 31, 1991;65(5):859-73.
Notice of allowance dated Sep. 1, 2016 for U.S. Appl. No. 14/128,354.

* cited by examiner

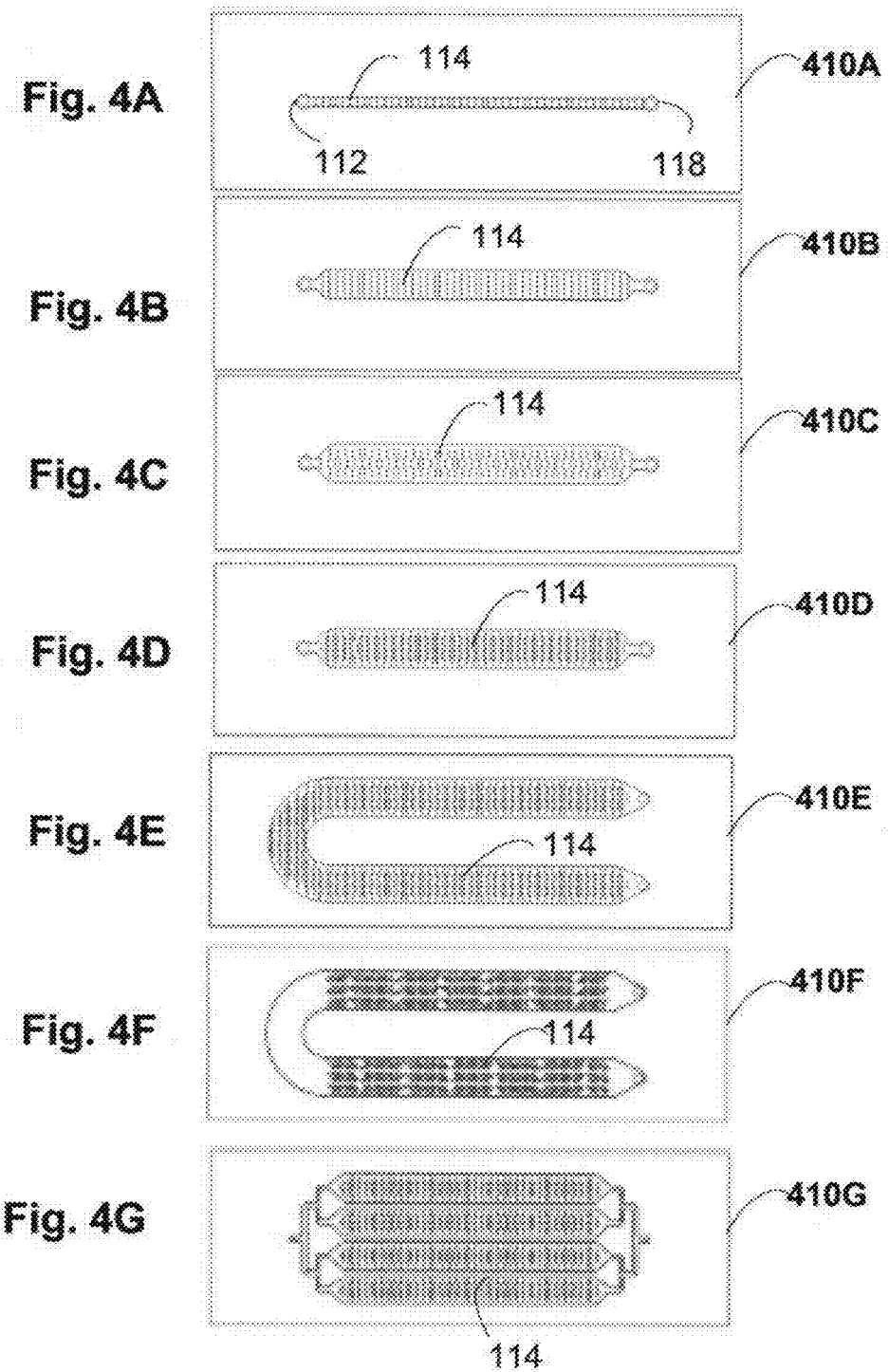

COLLECTION AND CONCENTRATION SYSTEM FOR BIOLOGIC SUBSTANCE OF INTEREST AND USE THEREOF

CROSS-REFERENCE TO RELATED APPLICATIONS

This application claims benefit of U.S. provisional patent application Ser. No. 61/719,491, filed Oct. 29, 2012, which is herein incorporated by reference.

FIELD OF THE INVENTION

This invention generally relate to systems and devices for collecting and concentrating a biologic substance of interest in a sample processing system. The system of the present invention can be used as a stand-alone device or in combination with other devices, including any device for processing biologic substances from a biologic sample. More specifically, the invention related to methods, components, parts, and devices in collecting and concentrating target proteins, cells and/or other materials of interest from biological samples for use in microfluidic systems.

BACKGROUND OF THE INVENTION

Great efforts have been devoted to the development of advanced systems and platforms to meet the growing demand of collecting, detecting, and processing biological samples from different sources, such as blood, biopsy samples, and tissue samples, etc. Among them, immunomagnetic systems (with magnetic nanoparticles and/or beads) and microfluidic chips (with special surface materials), to name a few, offer high sensitivity in collecting a biologic substance of interest (e.g., target proteins or cells of interest) from biological samples (such as tissues samples or blood samples drawn from a human subject, etc.).

Specificity of these systems and platforms normally lie in system design, which often takes advantage of binding affinity between targeted molecules of interests (such as targeted proteins present within a targeted cell or on the surface of a targeted cell) and specially-designed detection probes (e.g., antibodies, macromolecules, small molecules, nucleic acid and/or other materials). As an example, a microfluidic chip has been developed to detect circulating tumor cells (CTCs) in a human blood sample using anti-EpCAM antibody as a detection probe, which offers high specific binding affinity to epithelial cell adhesion molecules (EpCAM), as most circulating tumor cells are epithelial cells.

The shedding of cells, especially epithelial cells into blood circulation is an intrinsic property of a malignant tumor, and thus provides important information with regard to disease stage diagnosis, monitoring of treatment plans, and ultimate survival of cancer patients. For example, it was found that the number of some types of cells (e.g., circulating rare cells (CRCs), circulating tumor cells (CTCs), etc.) and other biological substance present in human blood samples are correlated with cancer metastasis (e.g., the aggressiveness of the tumor cells) as well as the efficacy of cancer therapy.

However, for most cancers, the corresponding circulating tumor cells (CTCs) shed in blood are very scarce, making it very difficult and technically challenging to detect, isolate, and collect these CTCs. Even for patients with late stage metastatic cancer, the number of CTCs present in blood may be as few as one CTC per $10^9$ blood cells. An enrichment process is necessary. In addition, there is a need to remove nonspecific binding of blood cells and other substances to improve detection sensitivity and specificity.

Furthermore, major bottleneck of most systems for rare cell detection lies in imaging techniques after targeted biologics of interest (e.g., rare cells or CTCs) are collected. Most immunomagnetic systems and microfluidic platforms for collecting target proteins or cells require bulky and expensive equipment, such as automated staging microscopes, automated scanners (e.g., for scanning and autofocusing in microfluidic channels) and/or readers (e.g., for quantitating scanned images). Moreover, a minimum of several hours of labor-intensive manual inspection of collected biological samples and/or images by a trained specialist may still be required.

Therefore, there is a need for a simplified and less expensive system to collect and concentrate a biologic substance of interest for various applications, such as disease diagnosis, disease treatment monitoring, and drug screening.

SUMMARY OF THE INVENTION

This invention generally relate to devices for collecting and concentrating target biologics for microfluidic applications. More specifically, the invention related to method and system for collecting and concentrating cells, such as rare cells (e.g., circulating rare cells (CRCs), circulating tumor cells (CTCs), etc.), proteins, and other biologic substance of interest, which may be present in various biologic samples.

In one embodiment, a system for processing a biologic substance of interest from a biologic sample includes a sample inlet configured to receive the biologic sample, a collection device connected to the sample inlet, a concentration device in fluid communication with the collection device, and a sample outlet. In another embodiment, a biologic sample processing system having a collection device and a concentration device integrated together for collecting and concentrating a biologic substance of interest from a biologic sample is provided. In still another embodiment, the concentration device of the system is configured to receive the biologic substance of interest from the collection device and concentrate the biologic substance of interest.

In still another embodiment, a method is provided to process a biologic substance of interest from a biologic sample using a system having a sample inlet, a collection device, a concentration device in fluid communication with the collection device, and a sample outlet. The biologic substance of interest is present at a first concentration within the biologic sample and can be received by the collection device via the sample inlet to interact with a bioactive composition, which is coupled to a nonfouling composition (e.g., by coupling to a linker composition) to form into a surface coating. The surface coating may comprise the bioactive composition, the nonfouling composition and the linker composition, and is attached to at least a portion of one or more surfaces of the collection device.

The method of processing the biologic substance of interest from the biologic sample generally includes capturing the biologic substance of interest present at a first concentration using the collection device of the system, releasing the biologic substance of interest from the collection device, and delivering the biologic substance of interest at a second concentration to the concentration device, and further increasing the concentration of the biologic substance of interest to a third concentration.

In one aspect, the third concentration is greater than the first concentration. In another aspect, the third concentration is greater than the second concentration. In still another aspect, the biologic substance of interest is released from the collection device via introducing air bubbles within the collection device. In one embodiment, the method may further include discarding one or more unwanted components from the biologic sample. In another embodiment, the method may further include confining the biologic substance of interest to a concentration region, and/or filtering a fluidic solution through one or more membrane-filtration elements positioned within the concentration device, wherein the fluidic solution comprises the biologic substance of interest.

In another embodiment, the method may further include culturing the biologic substance of interest in a culture medium. In addition, the method may further include performing one or more assays, including, but not limited to, one or more detection, characterization, enumeration, immunostaining, inspection, imaging, culturing, molecular analysis, combinations thereof, and/or other qualitative and quantitative assays to analyze the obtained biologic substance of interest.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 4A illustrates a top view of one embodiment of an exemplary collection device useful in a system of FIGS. 1A-1C, the collection device having a plurality of microstructures formed into a lined pattern.

FIG. 4B illustrates a top view of another exemplary collection device having a plurality of microstructures formed into a plurality of lines, which in turn formed into a pre-designed lined pattern according to another embodiment of the invention.

FIG. 4C illustrates a top view of another collection device having a plurality of microstructures formed into a plurality of pre-arranged lines, which in turn formed into another pre-designed lined pattern according to another embodiment of the invention.

FIG. 4D illustrates another embodiment of a top view of another exemplary collection device having a plurality of microstructures formed into a plurality of pre-arranged lines, which in turn formed into yet another pre-designed lined pattern.

FIG. 4E illustrates still another embodiment of a top view of an exemplary collection device having a plurality of microstructures formed into a plurality of pre-arranged lines, which in turn formed into a horseshoe-like pattern.

FIG. 4F illustrates yet another embodiment of a top view of an exemplary collection device having a plurality of microstructures formed into a plurality of pre-arranged herring bone-like lines, which in turn formed into a horse shoe-like pattern.

FIG. 4G illustrates yet another embodiment of a top view of an exemplary collection device having a plurality of microstructures formed into a plurality of pre-arranged lines, which in turn formed into a pattern of multiple lines, with their inlets and outlets inter-connected.

DETAILED DESCRIPTION

Figure 1A:
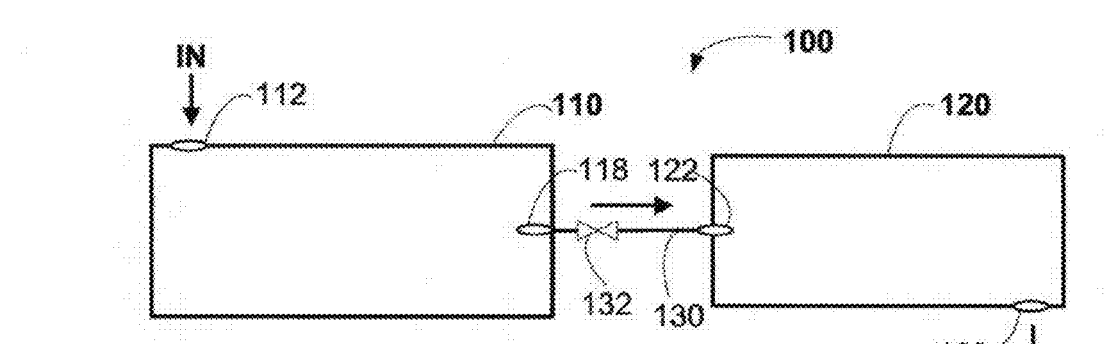
FIG. 1A is a schematic of a collection device and a concentration device integrated in a system of capturing and concentrating a biologic substance of interest according to one embodiment of the invention.

Embodiments of the invention generally provide a system and a method thereof for collecting a biologic substance of interest, which may be present in a biologic sample at a low first concentration. The biologic substance of interest may be captured by a collection device positioned within the system, and unwanted components within the biologic sample are removed (e.g., by washing and flushing the system with washing buffers, solutions, and other fluids, etc.). After being captured within the collection device, the biologic substance of interest can be released and collected in relatively high purity into a second concentration, which is greater than the first concentration (e.g., at least 10×-50,000× enrichment in concentration and/or purity). In addition, the biologic substance of interest is delivered into a concentration device, which is coupled to the collection device within the system, and the biologic substance of interest can be further concentrated into a third concentration. Accordingly, after processing the biologic sample through the system integrated with at least one collection device and at least one concentration device, the biologic substance of interest is obtained at the third concentration, which is much greater than the first concentration as well as in a highly purified state, thereby facilitating further analysis of the obtained biologic substance of interest. The system provided herein is in a simple and flexible format to offer the advantages of small scale, applicability to various biologic substance of interest, ease in handling without the need for additional and complicated instruments, among others.

In one aspect, the system is a two-part microfluidic system with liquids, fluids, solutions, etc., flowing through one or more flow paths of a plurality of microstructures within a microfluidic collection device (e.g., a microfluidic chip, etc.) and then into one or more flow paths of a plurality of microfeatures within a microfluidic concentration device, taking advantages of hydrodynamic forces to drive the flows of the biologic substance of interest and various components of the biologic sample through the collection device and the concentration device within the system. In another aspect, the concentration device may include one or more membrane filtration elements, target-concentration regions, outlet channels, or combinations thereof arranged to entrap and concentrate the biologic substance of interest.

In one embodiment, a microfluidic concentration device is coupled to a microfluidic collection device directly to form an integrated enclosed system. In another embodiment, a concentration device is connected to a microfluidic collection device via a conduit with an optional valve. For example, unwanted materials (e.g., unwanted proteins, serum, cells, and other components from the biologic sample and unwanted wastes, buffers and solutions, among others) can be diverted via a three-way valve out of the system, thus being separated and discarded, and not being flown into the concentration device, thereby ensuring the quality of the obtained biologic substance of interest. In addition, depending on the type of the valve coupled to the conduit between a collection device and a concentration device, the flow rate of any fluids or solutions delivered from the collection device into the concentration device can be adjusted.

Suitable biologic substance of interest (or target biologic substance) which can be used in a system as described herein may include, but is not limited to, rare cells, circulating rare cells (CRCs), circulating fetal cells, tumor cells (e.g., circulating tumor cells (CTCs), epithelial tumor cells, epithelial marker-negative tumor cells, and the like), stem cells (e.g., circulating stem cells, tumor stem cells, liver stem cells and bone marrow stem cells, etc.), cells in bone marrow, cells in urine, stool or other body fluids, epithelial cells (e.g., circulating epithelial cells and the like), circulating endothelial cells, trophoblastic cells, bacteria, virus, viral surface proteins, proteins, nucleic acids, fetal cells, endothelial cells, and combinations thereof, among others. Suitable biologic sample includes, but is not limited to, blood sample, tissue sample, bone marrow, urine, feces, biopsy sample, and combinations thereof, among others, and is obtained from sources including human or animals. Unwanted components within the biologic sample may include, but are not limited to, white blood cells, lymphocytes, leukocytes, red blood cells, serum proteins, platelets, various blood cells or blood components, non-target proteins, washing buffers or solutions, reagents, and any non-target biologic substance, among others.

FIG. 1A illustrates a system 100, which generally includes a collection device 110 and a concentration device 120 integrated together and in fluid communication for capturing, collecting and concentrating a biologic substance of interest. A biologic sample having a biologic substance of interest therein is delivered in fluid, liquid, solution or other forms into the system 100 via a sample inlet 112, which is positioned on a portion of the collection device 110. The biologic substance of interest within the biologic sample can be captured on one or more surfaces within the collection device 110, washed, and then released out of the collection device via an outlet 118.

After being captured and released from the collection device 110, the biologic substance of interest can be delivered (for example, in fluidic flows and the like) via a conduit 130 into an inlet 122 of the concentration device 120. Optionally, one or more fluidic flows of the biologic substance of interest delivered into the concentration device 120 can be monitored or adjusted via a valve 132 positioned on the conduit 130. The biologic substance of interest is flown through the concentration device 120 to be concentrated to a higher concentration and then delivered out of the system 100 via a sample outlet 128.

Figure 1B:
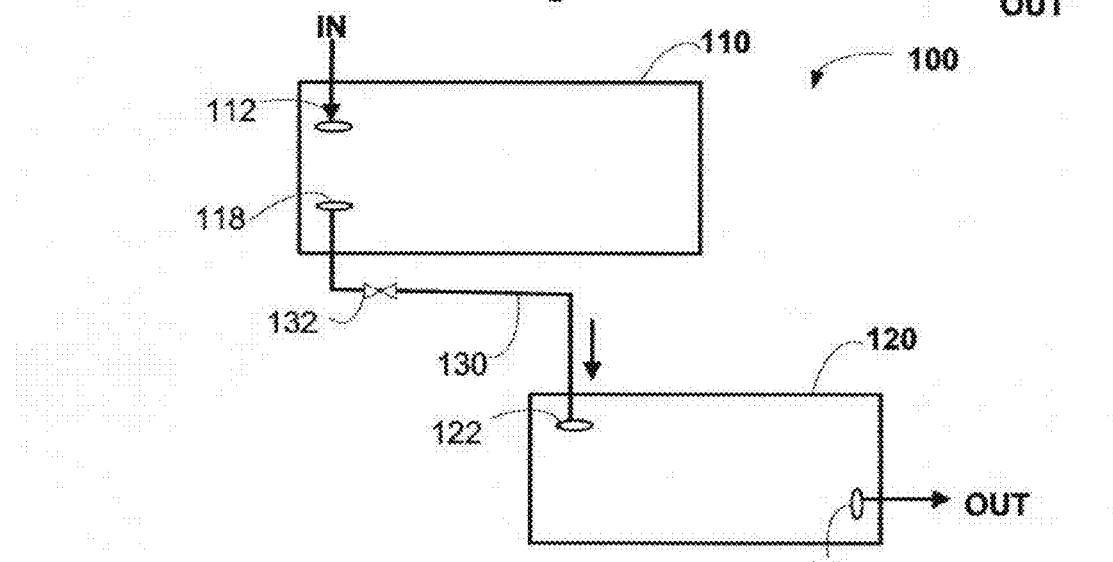
FIG. 1B is a schematic of another embodiment of an exemplary system of collecting and concentrating a biologic substance of interest.
Figure 1C:
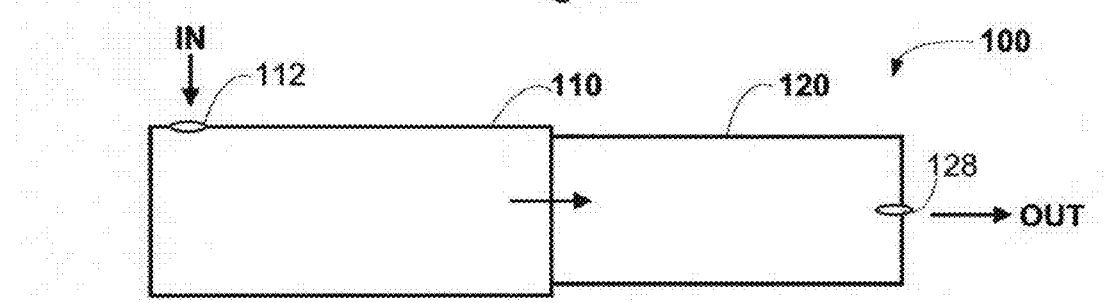
FIG. 1C is a schematic of still another embodiment of another exemplary system of collecting and concentrating a biologic substance of interest.

FIGS. 1B-1C represent additional examples in integrating the collection device 110 and the concentration device 120 into the system 100 for collecting and concentrating a biologic substance of interest according to various embodiments of the invention. In FIG. 1B, it is contemplated that the positioning of the collection device 110 and the concentration device 120 can vary as long as the two devices are in fluid communication (e.g., coupled together via the conduit 130). In FIG. 1C, the collection device 110 and the concentration device 120 are coupled together without the need for a conduit and fluids from the collection device 110 can be flown and delivered into the concentration device 120 directly, i.e., the collection device 110 is in direct communication with the concentration device 120. The materials for the system 100 are not limited, and the system 100 can be made from a variety of materials, including but not limited to, polydimethyl-siloxane (PDMS), polyethylene (PE), polycarbonate (PC), polystyrene (PS), polymethyl methacrylate(PMMA), cyclic olefin copolymer (COC), silicon, glass, thermoplastics materials and the like.

In addition, the sample inlet 112 and the outlet 118 can be designed to be positioned at various locations within the collection device 110 (e.g., at opposite ends as shown in FIG. 1A) or around the same portion (e.g., as shown in FIG. 1B, for ease of handling the system 100). Similarly, the locations of the inlet 122 and the sample outlet 128 can be designed in different portions of the concentration device (e.g., as shown in FIGS. 1A-1B) or around the same portion to help in handling the system 100.

In one aspect, the collection device 110 includes one or more surfaces (e.g., glass surface, plastic surfaces, etc.) with a surface coating attached to a portion thereon. In another aspect, the surface coating includes a nonfouling composition (e.g., a lipid, a lipid bilayer, a surface lipid bilayer, lipid vesicles, etc.) and a bioactive composition. The bioactive composition of the surface coating specifically interacts with the biologic substance of interest present within the biologic sample such that the collection device 110 selectively collects the biologic substance of interest from the biologic sample delivered therein.

The collection device 110 of the system 100 includes one or more surfaces having a plurality of microstructures 114 arranged in one or more patterns (e.g., one or more lines, a horseshoe pattern, a herringbone pattern, one or more herringbone patterned lines, one or more lines of clustered microstructures, and various combinations thereof, etc.) thereon. In one aspect, the collection device 110 is a microfluidic device. In another aspect, the system 100 further comprises a conduit 130 connected to the outlet 118 of the collection device 110 and the inlet 122 of the concentration device 120. In another aspect, the conduit 130 between the collection device 110 and the concentration device 120 is coupled to the valve 132 capable of being configured to discard one or more unwanted components, (e.g., serum, non-specific components, and other unwanted cells and proteins, etc.) from the biologic sample. For example, a majority portion of unwanted components can be discarded and prevented from entering into the concentration device 120. The biologic substance of interest can be released form the surface coating and carried to and received by the concentration device 120. One example of the surface coating is a lipid bilayer.

In one aspect, the concentration device 120 of the system 100 includes a plurality of microfeatures 124 (shown in FIGS. 6A, 6B, 6E, 6F) arranged in one or more patterns positioned on one or more surfaces of concentration device 120 and configured to concentrate the biologic substance of interest 518 (shown in FIGS. 5A, 6A-6H) received by the concentration device 120 from the collection device 110. In another aspect, the plurality of microfeatures 124 within the concentration device 120 is arranged in a pattern including, but no limited to, one or more lines, a horseshoe pattern, a herringbone pattern, one or more herringbone patterned lines, one or more lines of clustered microfeatures, and various combinations thereof, among others.

In an alternative embodiment, the concentration device 120 of the system 100 includes a target-concentration region 610 (shown in FIGS. 6B and 6G) adapted to collect the biologic substance of interest 518 near the sample outlet 128. In one aspect, the target-concentration region 610 is a well having a surface area of between about 1 mm$^2$ and about 100 mm$^2$ (e.g., between about 1 mm$^2$ and about 20 mm$^2$).

In another alternative embodiment, one or more surfaces of the concentration device 120 of the system 100 include one or more filtration elements 126, such as a filer membrane. In one aspect, at least one filtration element is spatially arranged near the sample outlet 128. In another aspect, at least one filtration element 126 includes a filter membrane sandwiched between two adjacent chambers surrounded by one or more chamber walls being made of a material selected from the group consisting of polydimethylsiloxane (PDMS), polymethyl methacrylate (PMMA), polyethylene (PE), polycarbonate (PC), polystyrene (PS), cyclic olefin copolymer (COC), silicon, glass, thermoplastics materials, and combinations thereof.

In yet another alternative embodiment, the concentration device of the system includes one or more channels spatially arranged near the sample outlet. Another alternative embodiment of the invention provides the integration of one or more membrane-filtration elements with at least one or a combination of a plurality of microfeatures, a target-concentration region, one or more channels within the concentration device of the system.

Figure 2:
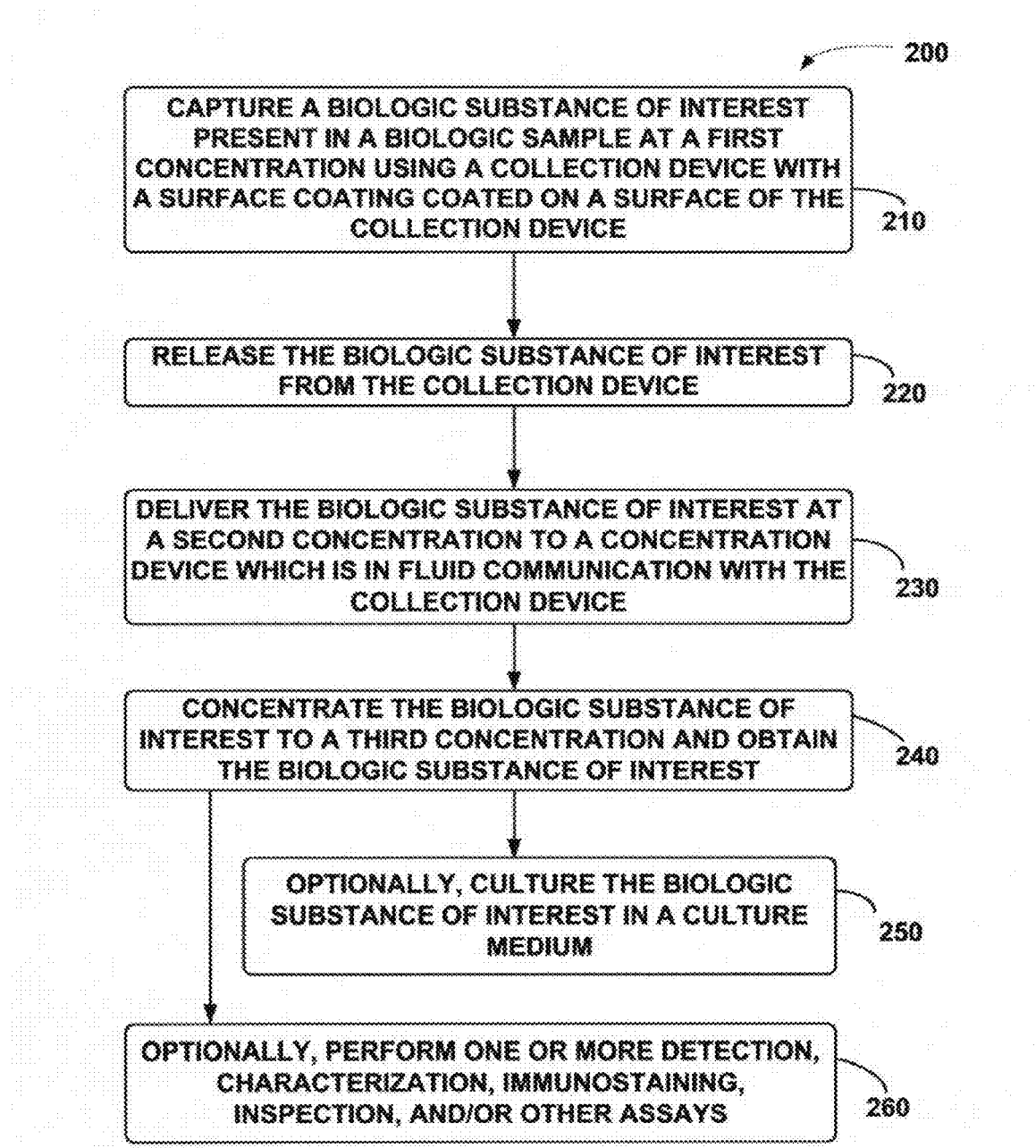
FIG. 2 illustrates one embodiment of a flow chart of a method of collecting and concentrating a biologic substance of interest using a system having at least one collection device and at least one concentration device.

FIG. 2 illustrates a method 200 of collecting and concentrating a biologic substance of interest using the system 100 as described herein. Firstly, at step 210 of the method 200, the biologic substance of interest present at a first concentration within the biologic sample can be captured by a surface coating positioned on one or more surfaces within the collections device 110. In general, the initial first concentration of the biologic substance of interest present in a biologic sample may be so low that the biologic substance of interest cannot be detected by regular detection assays without enrichment through the system 100 described herein or any other capturing or enrichment process. For example, it is estimated that as few as one circulating tumor cell (CTC) per $10^9$ blood cells is present in patients with metastatic cancer. It has been shown that about four (4) CTCs may be present in about 7.5 ml of a blood sample from a Stage IV Metastatic cancer patient. In addition, rare cells, such as circulating tumor cells are normally absent in healthy subjects. Here, the system 100 provides a highly sensitive system to collect and concentrate rare cells, such as CTCs, which is present in very low concentration in blood samples of cancer patients.

The surface coating within the collection device 110 may generally include a nonfouling composition and a bioactive composition. The surface coating can be positioned, incorporated, or attached to a surface of a substrate, which may include glass or plastic-containing materials within slides, plates cell culture dishes, microfluidic channels, microfluidic chips, filtration filter, capillaries, tubes, beads, nanoparticles or the like.

In general, the bioactive composition provides a binding moiety selective for the detection and binding of the biological substance of interest through molecular recognition, chemical affinity, or geometrical/shape recognition. Examples of the binding moiety for the detection of the biological substance include, but are not limited to, synthetic polymers, molecular imprinted polymers, extracellular matrix proteins, binding receptors, antibodies, DNA, RNA, antigens or any other surface markers which present high affinity to the biological substance.

In one example, an antibody, such as anti-EpCAM, (Epithelial Cell Adhesion Molecule) can be used as the bioactive composition for the detection of the biological substance of interest, such as, CRCs and CTCs, which are epithelial cells not normally present in blood samples of healthy subjects, but may be present in blood samples of cancer patients, because of shedding of tumor epithelial cells into blood circulation. One exemplary antibody is the anti-EpCAM membrane protein antibody (commercially available from many sources including R&D Systems, MN, USA), which provides high specificity for CTCs because EpCAM is frequently overexpressed in the lung, colorectal, breast, prostate, head and neck, and hepatic malignancies, but is absent from hematologic cells. Another exemplary antibody is Anti-HER2. Other antibodies specific for cell surface makers, viral proteins, and various target proteins can be used to be coupled to a nonfouling composition to form into a surface coating coated on one or more surfaces within the collection device 110.

The nonfouling composition within a surface coating is chosen to provide its binding affinity to a surface of the collection device 110 and its high mobility on the surfaces of the collection device 110, as well as its low affinity to proteins. For example, the high mobility and fluidic nature of the nonfouling composition can enhance specific and collaborative binding between the bioactive composition and the biologic substrate substance of interest (e.g., between an antibody and its specific surface protein antigen and the like) and reduces adsorption of unwanted other proteins on the surface of the collection device 110, thus enables the use of low shear force through various fluid flow paths within the collection device 110 for purification of the biologic substrate substance of interest. The nonfouling composition can be coupled to a surface, such as one or more solid surfaces of the collection device 110, and occupies the surfaces of the collection device 110 to prevent non-specific binding and adsorption of unwanted components (e.g., blood cells and serum proteins, etc., from a blood sample) onto the surfaces of the collection devices. The nonfouling composition also acts as a "lubricating" surface agent such that low shear stress of a fluid flow can be used to wash away, remove, and or discard unwanted non-specific blood cells from the surface coating, while making the biological substance of interest remain intact and bound to the surface coating.

For example, the nonfouling composition can be a lipid, such as supported lipid bilayers (SLB), including 1,2-dioleoyl-sn-glycero-3-phosphoethanolamine-N-(cap biotinyl) (sodium salt) (b-PE) and 1-Palmitoyl-2-oleoyl-sn-glycero-3-phosphocholine (POPC), among others. Other examples of nonfouling compositions include lipid bilayers, liposomes, polypeptides, polyelectrolyte multilayers (PEM), polyethylene glycol (PEG), hydrogel polymers, extracellular matrix proteins, carbohydrate, polymer brushes, Zwitterionic Materials (e.g., poly(sulfobetaine) (pSB) and poly(carboxybetaine) (pCB)), etc.), small organic compounds, and combinations thereof. Suitable PEM may include poly-L-lysine/poly-L-glutamic acid (PLL/PLGA) copolymer, poly-L-lysine/poly-L-aspartic acid copolymer, or similar counterionic polyelectrolytes. Suitable polymer brush may include copolymer of [2-(acryloyloxy)ethyl]trimethyl ammonium chloride (TMA) and 2-carboxy ethyl acrylate (CAA). Suitable PEG may have a molecular weight ranging form 100 to 100,000 and exhibits a nonfouling property (low affinity to protein, repellant or resistant to protein). The nonfouling composition generally have a low affinity for protein (repellant or resistance to protein), which can be explained by the presence of its neutral and Zwitterionic phosphatidylcholine head groups in a wide pH range, and the formation of an aqueous thin film between the hydrophilic lipid head groups and the bulk solution (see Johnson et al., Biophy J 1991, 59:289-94). Generally, the surface coating may include a single layer or multiple layers of the nonfouling composition. In addition, the non-fouling composition may form into a thickness from a few nanometers up to hundreds microns.

The nonfouling composition and the bioactive composition may be coupled together or linked directly (e.g., via one or more of functional groups of the nonfouling composition and the bioactive composition, thus forming a binding pair) or indirectly (e.g., via a linker composition). For example, the nonfouling composition, the bioactive composition, and the linker composition may have compatible functional groups, which are capable of linking these compositions together via covalent binding interactions, non-covalent interactions, electrostatic interaction, hydrophilic-hydrophilic interaction, polar-polar interaction, DNA-complementary DNA binding interaction, magnetic force, or combinations thereof.

Functional groups that may be present on the nonfouling composition, the bioactive composition, and/or the linker composition prior to covalent binding include, but are not limited to, hydroxy groups, amine groups, carboxylic acid or ester groups, thioester groups, aldehyde groups, epoxy or oxirane groups, hyrdrazine groups and thiol groups. Other functional groups or moieties that may be present prior to non-covalent interactions include specific binding/recognition pairs, such as specific binding recognition of biotin, avidin, streptavidin, DNA, RNA, ligand, receptor, antigen and antibody with a first member of a binding pair present on the bioactive composition and a second member of the binding pair present on the nonfouling composition and/or the linker composition. One example of a specific binding pair employs complimentary DNA fragments, where a first DNA strand is attached to the bioactive composition and the second DNA strand partially or completely complementary to the first DNA strand is attached to the linker composition or the nonfouling composition. A suitable DNA length can be 15, 20, 25, 35, 50, 100 or more bases in length. The functional groups on the linker composition can also be a cleavable functional group, including, but not limited to, a photosensitive functional group cleavable by ultraviolet irradiation, an electrosensitive functional group cleavable by electro pulse mechanism, a magnetic material cleavable by the absence of the magnetic force, a polyelectrolyte material cleavable by breaking the electrostatic interaction, an DNA cleavable by hybridization, and the like.

Figure 5A:
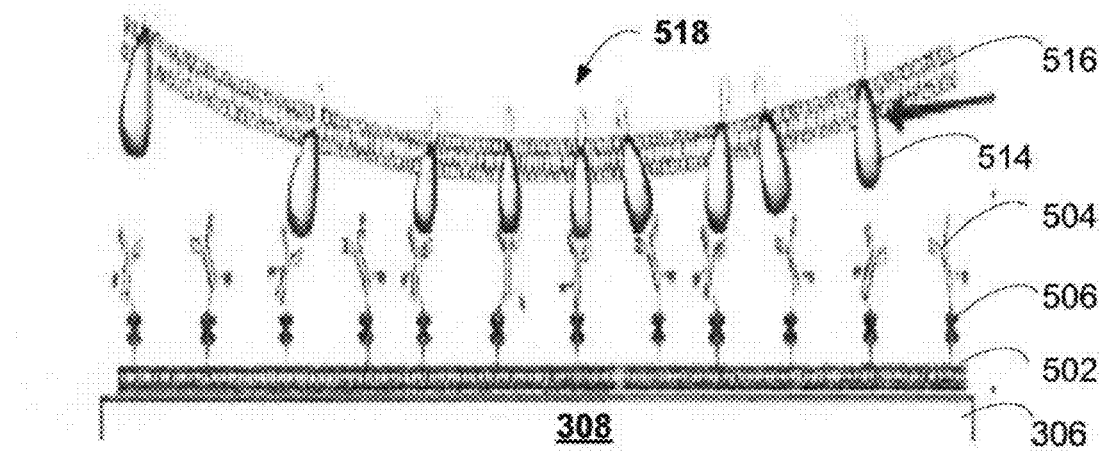
FIG. 5A shows a schematic of an exemplary surface coating attached on a surface of a collection device to interact with a biologic substance of interest present in a biologic sample according to various embodiments of the invention.
Figure 5B:
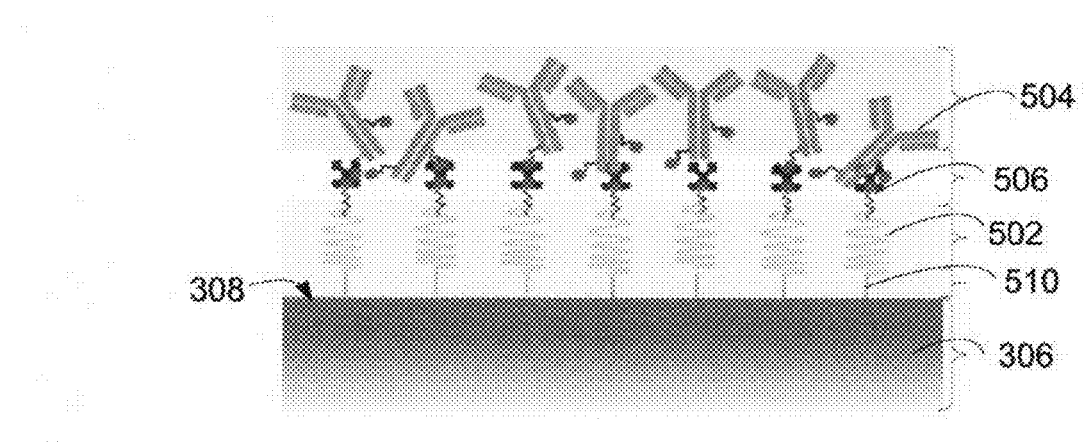
FIG. 5B shows a schematic of another exemplary surface coating attached on a surface of a collection device to interact with a biologic substance of interest present in a biologic sample according another embodiment of the invention.

Two examples of the surface coating are shown in FIGS. 5A-5B. Both examples are useful in capturing circulating rare cells (CRCs), such as circulating tumor cells (CTCs), circulating stem cells, etc., from a biologic sample, such as a blood sample. In FIG. 5A, the surface coating generally includes a bioactive composition 504, a linker composition 506, and a nonfouling composition 502. The surface coating is attached on a solid surface 308 of a substrate 306 within the collection device 110 to interact with a biologic substance of interest (e.g., a target cell 518) present in a biologic sample according various embodiments of the invention.

As shown in FIG. 5A, the bioactive composition 504 is contemplated and designed to bind specifically to cell surface proteins 514 of a biologic substance of interest, such as the target cell 518 (e.g., CRCs, CTCs). The target cell 518 is normally enclosed by membrane layers 516 (e.g., an inner membrane layer and an outer membrane layer) with cell surface proteins 514 located on its membrane surface. The thickness of the bioactive composition 504 does not affect the function or the performance of the surface coating. In one embodiment, the nonfouling composition 502 and the bioactive compositions 504 are joined by one example of the linker composition 506 using biotin/avidin as the binding pair of functional groups. In another embodiment, the nonfouling composition 502 and the bioactive composition 504 are joined by EDC/NHS. In still another embodiment, the nonfouling composition 502 and the bioactive compositions 504 are joined by sulfo-SMCC.

Exemples of the cell surface proteins 514 may include EpCAM membrane proteins, HER2 proteins, cancer markers, cytokines, chemikines, cell surface receptors, cytokine receptors, and the like. One example of the bioactive composition 504 is anti-EpCAM antibody, such as biotinylated EpAb4-1 monoclonal antibody or biotinylated OC98-1 monoclonal antibody generated by being raised against a peptide sequence of EpCAMmembrane proteins. Another example of the bioactive composition 504 is biotinylated anti-HER2 antibody, having a biotin functional group. Where the bioactive composition 504 is a biotinylated antibody, the linker composition 506 may be strepavidin (SA), which may interact with the biotin binding moiety of the bioactive composition 504. In addition, the linker composition is coupled to the nonfouling composition 502. For example, strepavidin (SA) can be coupled to the nonfouling composition 502, for example, supported lipid bilayer (SLB). The nonfouling composition 502 are attached to the solid surface 308 of the substrate 306 within the collection device 110.

FIG. 5B shows another exemplary surface coating attached on the solid surface 308 of the substrate 306 within the collection device 110 to interact with a biologic substance of interest present in a biologic sample. In FIG. 5B, the surface coating includes the bioactive composition 504 coupled to the nonfouling composition 502 via the linker composition 506, and may further include a surface linker 510 to link the nonfouling composition 502 to the solid surface 308.

The surface linker 510 may include functional groups capable of non-covalent, covalent or a combination thereof to attach directly to functional groups present in the nonfouling composition 502 and/or the solid surface 308 of the substrate 306. For example, the surface linker 510 may include a cleavable functional group, such as a photosensitive functional group cleavable by ultraviolet irradiation, an electrosensitive functional group cleavable by electro pulse mechanism, a iron or magnetic material in which the absence of the magnetic force releases the nonfouling composition 502, a polyelectrolyte material cleavable by breaking the electrostatic interaction, an DNA cleavable by hybridization, and the like. Examples of the surface linker 510 include, but are not limited to, silane, aminopropyltriethoxy silane, aminopropyltrimethoxy silane, silane-PEG-NH2, silane-PEG-N3 (PEG molecular weight is about 1000 to about 30000 daltons) and silane-PEG biotin.

A surface coating with a linker composition can be formed by coupling the nonfouling composition (e.g., SLB or PEG) with appropriate functional groups (e.g., biotin) and attaching a corresponding pair of a functional group (e.g., streptavidin) on the linker composition to the functional group on the nonfouling composition (e.g., biotin). Next, the bioactive composition is formed with its functional group (e.g., biotin) attached to the functional group on the linker composition (e.g., streptavidin). A surface coating without a linker composition can be formed by forming the nonfouling composition with appropriate functional group (e.g., NGPE), and forming and attaching the functional group (e.g., primary amine) on the bioactive composition to the functional group on the nonfouling composition.

Referring back to FIG. 2, at the end of step 210, once the biologic substance of interest is captured by the collection device 110 through its interaction with the bioactive composition of the surface coating coated on the one or more surface of the collection device 110, unwanted components within the biologic sample are washed away from the collection device 110 (e.g., through a buffer rinse, flushing with washing buffers or other solutions, such as phosphate-buffered saline (PBS) solutions, fluids, etc.,) and delivered out of the collection device 110 via the outlet 118.

The biological substance of interest bound and captured on the surface coating can be further purified by removing the unwanted non-specifically bound cells and unwanted blood components on or near the nonfouling composition. Because the nonfouling composition is chosen to have low adhesion affinity for non-target specific cells and other blood components, a low shear stress (e.g., less than about 15 dyne/cm$^2$) may be sufficient to remove non-specific blood cells and other blood components near the nonfouling composition, which is attached to one or more surfaces of the collection device 110, while the biological substance of interest remains on the surface coating and indirectly coupled to the surfaces of the collection device 110, not being washing away. Rinsing the surface coating with a buffer solution causes a shear stress sufficient to remove non-specifically bound materials on the nonfouling composition.

Results from testing optimal shear stress of a flow of buffer wash at about 3.3 dyne/cm$^2$ show about 80% of non-specific blood cells (i.e. white blood cells) can be removed while none of the biological substance of interest (e.g., HCT116 cancer cells) are removed from the surface coating. Not wishing to be bound by theory, it is contemplated that, by having the microstructures 114 arranged in specific pattern and connected together to form fluid flow within the collection device, a disturbed flow of blood, body fluid or biological samples can be created while passing the collection device and the capture rate of the biological substance of interest can be enhanced.

At step 220, the biologic substance of interest is then released from the collection device 110. In one example, the biologic substance of interest is released from the collection device 110 by introducing air bubbles in solutions or oil phases to break the coupling of the nonfouling composition and the bioactive composition. In another example, the release is done by breaking the coupling of the nonfouling composition and the bioactive composition, such as the use of UV radiations.

If the nonfouling composition 502 comprises a lipid or a mixture of lipid, the captured biological substance can be released by introducing an air bubble solution. For example, the biological substance of interest, such as CRC and CTC, can bind to the bioactive composition 504, whereas other cells were repelled by the nonfouling composition 502. As the air bubble approach the lipid bilayer of the nonfouling composition 502, the hydrophobic tails of the lipid bilayer are turned upside down due to its high affinity with the air in the air bubbles, which is also hydrophobic. This breaks up the hydrophilic-hydrophilic interaction at the surface of the lipid bilayer and allows the air bubble to "lift off" the top layer of the lipid bilayer, carrying together with it the CTC target cell bound on the bioactive composition 504.

If the nonfouling composition comprises a composition other than a lipid or a mixture of lipid, the captured biological substance can be released by breaking the cleavable functional group in the linker composition or in the surface linker. One example of a release mechanism may be used in a surface coating having a linker composition with a cleavable functional group. When the target CTC cell is bound to the bioactive composition, and the surface coating is attached to a solid substrate, unwanted non-target cells can be repelled by the nonfouling composition. The surface coating having a linker composition with a cleavable functional group can be irradiated with, for example, 365 nm ultraviolet light, which cleaves the cleavable functional group on the linker composition and release the CTC for subsequent analysis.

The biological substance of interest can also be released by other mechanisms. For example, if the linker composition or the surface linker comprises an electrosensitive functional group, the biological substance can be released by electro pulse mechanism. If the linker composition or the surface linker comprises a magnetic material, the absence of the magnetic field or force will release the biological substance. If the linker composition or the surface linker comprises a PEM, the biological substance can be released by changing the electrostatic interaction between the layers. If the linker composition or the surface linker comprises a DNA piece, the biological substance of interest can be released by DNA hybridization.

At step 230, the biologic substance of interest released from the collection device 110 is delivered into the concentration device 120 by passing through the outlet 118 and the inlet 122. The delivery of the biologic substance of interest may be assisted by one or more flow of fluids, buffers or solutions to carry the biologic substance of interest in a second concentration into the concentration device 120. In general, the second concentration of the biologic substance of interest is much greater than the initial first concentration; for example, there could be as high a 10 fold to 50,000 fold difference in terms of number of rare cells versus total nucleated cells.

At step 240, the biologic substance of interest can be concentrated by the concentration device 120 to a third concentration, thereby obtaining the biologic substance of interest at high purity and quantity. In one embodiment, the third concentration is greater than the first concentration of the biologic substance of interest present in the biologic sample. In another embodiment, the third concentration of the biologic substance of interest obtained from the concentration device 120 is greater than the second concentration of the biologic substance of interest released from the collection device 110. The concentrations in these embodiments may refer to the number of rare cells versus total nucleated cells or the number of rare cells per unit liquid volume.

Optionally, at step 250, the obtained biologic substance of interest can be cultured, for example, in a serum-containing culture medium supplemented with antibiotics (such as penicillin, streptomycin, gentamicin, etc.). For example, the target cell 518 within the concentration device 120 can be incubated with 5 mM of EDTA buffer solution (other buffers can also be used) at 37° C. for 5 to 10 min and then released by flowing a culture medium into the system 100. In addition, trypsin or other proteases, enzymes, may be added in the solution for incubation. Alternatively, the target cells of interest can be directly released from the collector 110 by bubble flush and collected. The obtained target cells, together with a serum-containing culture medium and antibiotics (penicillin+streptomycin+gentamicin), can be placed onto a 48-well tissue cultured polystyrene plate for cell cultivation. Results have been obtained for culturing 18 target CTC cells (e.g., colo205 cells) for as long as at least 10 to 14 days. The results demonstrate the biologic substance of interest, such as target CTCs, obtained form the system 100 retain their viability for subsequent cell culture.

Additionally, at step 260, one or more detection, characterization, enumeration, immunostaining, inspection, imaging, culturing, molecular analysis, and/or other assays can be performed to further inspect and characterize the biologic substance of interest qualitatively and quantitatively. Exemplary assays include, but are not limited to, immnuofluorescent staining with biomarkers, PCR, qPCR, RT-PCR or next generation sequencing (NGS).

Figure 3A:
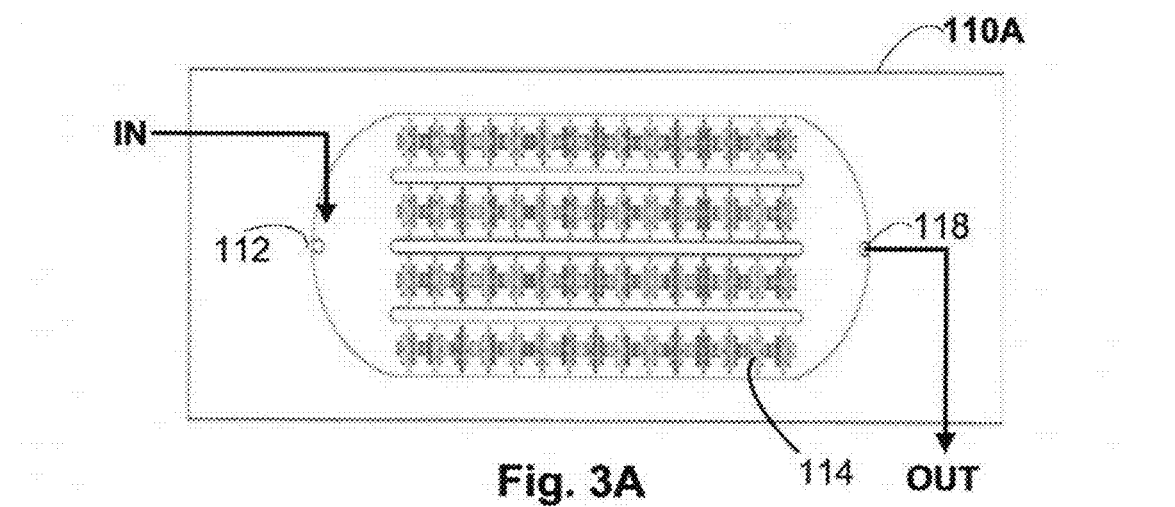
FIG. 3A is a top view of an exemplary collection device useful in a system of FIGS. 1A-1C for capturing and collecting a biologic substance of interest according to one embodiment of the invention.
Figure 3B:
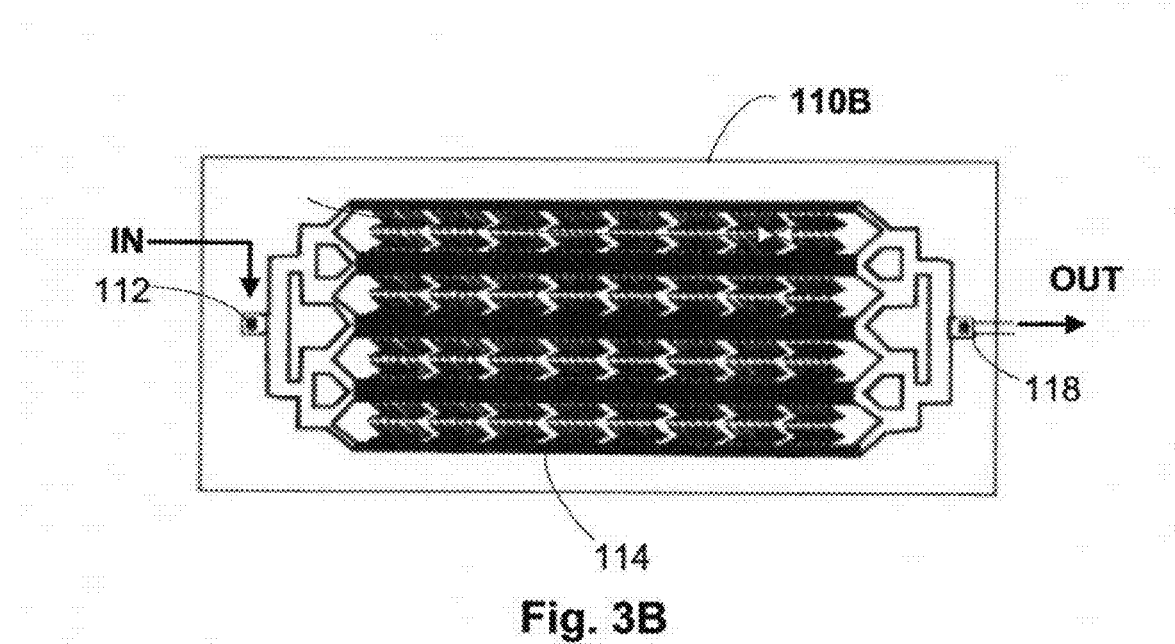
FIG. 3B is a top view of another exemplary collection device according another embodiment of the invention.

FIGS. 3A-3B provide top views of two examples of collection devices 110A, 110B, which can be positioned within the system 100 of FIGS. 1A-1C for capturing and collecting a biologic substance of interest. The collection devices 110A, 110B may include a plurality of microstructures 114 (e.g., trenchs, vias, holes, cavities, grooves, slanted grooves, mesa, and other features which may be in microsizes or other sizes, etc.). The microstructure 114 may be etched or engraved and formed on one or more surfaces of a collection device (e.g., the collection devices 110, 110A, 110B, etc.), and may be arranged in various patterns.

In FIG. 3A, the plurality of the microstructures 114 are formed and arranged in a lined pattern, e.g., clusters of microstructures 114 arranged in 4 lines. In FIG. 3B, the plurality of the microstructures 114 are formed and arranged in a lined herringbone pattern, e.g., clusters of microstructures 114 arranged in herringbone shape and formed into 2 lines, which are then connected in 4 groups.

Figure 3C:
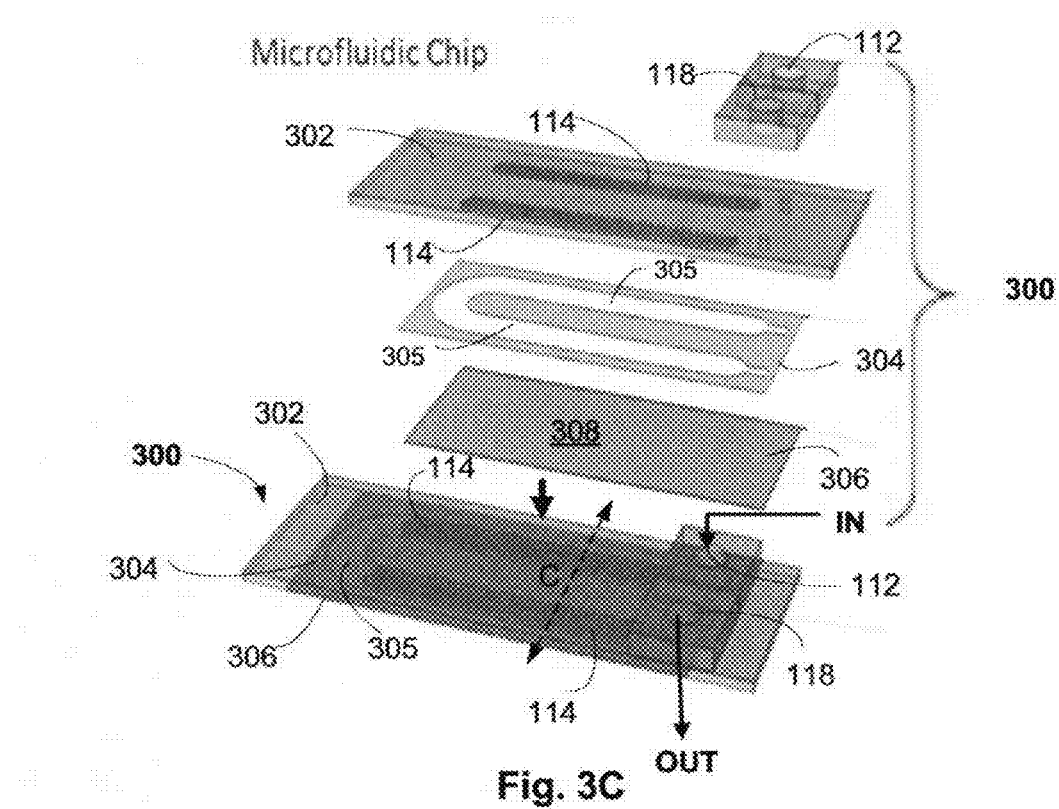
FIG. 3C illustrates a perspective view of the assembly of various components of an exemplary collection device according to one embodiment of the invention.

FIG. 3C illustrates a perspective view of the assembly of various components of a collection device, such as a microfluidic chip device 300. The microfluidic chip device 300 generally include the sample inlet 112, the outlet 118, coupled to a substrate 302 with a pattern of the microstructures 114 engraved thereon its surface. The substrate 302 is adhered to a substrate 306 together with an adhesive layer 304. For example, the bottom surface of the substrate 302 may be attached to the top surface of the substrate 306 with the adhesive layer 304 being sandwiched therebetween, thereby forming the height of a microfluidic flowing path (e.g., fluid flow channels formed within the collection device).

The substrates 302, 306 may be made of a material, including, but not limited to, hydroxylated poly(methyl methacrylate) (PMMA), glass, metals, plastics, silicon wafers, and a combination thereof, among others. The shape of the substrate 302, 306 may vary and may be planar, circular, or irregular. In the example of the nonfouling composition 502 comprises PEG which is functionalized with a surface linker silane, the solid surface 308 of the substrate 306 may include a material, such as silicon, glass, hydroxylated poly(methyl methacrylate) (PMMA), aluminum oxide, $TiO_2$ and the like. In addition, the substrates 302, 306 may include additional micro- or nano-structures, such as nanoparticles, nanowires, and a combination thereof.

The adhesive layer 304 is carved out in a shape corresponding to the pattern of the plurality of the microstructures 114 on a surface (e.g., the bottom surface) of the substrate 302 to accommodate the pattern of the plurality of the microstructures 114 and form into a plurality of sealed fluid channels (as shaped by the dimension of the plurality of the microstructures 114 and the thickness of carved out portion of the adhesive layer 304). For example, the adhesive layer 304 may be carved out in one or more patterns or shapes (e.g., a horseshoe shape as illustratively shown in FIG. 3C) to form one or more fluid channels 305. In one aspect, the pattern of the carved out portion of the adhesive layer 304 may correspond to the overall pattern and shape of the plurality of the microstructures 114 on the substrate 302. One example of the adhesive layer 304 is a 3M adhesive tape (available from 3M, USA) with a thickness of less than 0.1 mm, such as about 63 µm. Once the collection device is formed, the surface coating, with or without a surface linker, can be attached to one or more surfaces of one or more solid substrates (e.g., the surfaces of the substrates 302, 306 or the adhesive layer 304).

Figure 3D:
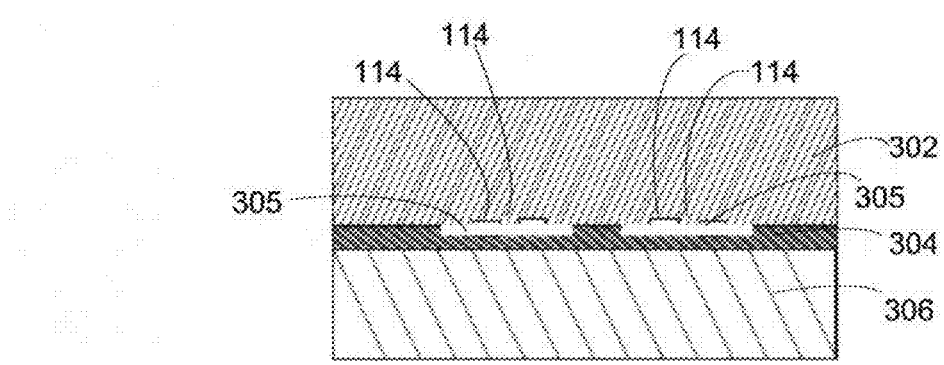
FIG. 3D is a cross-sectional view a microfluidic portion of an exemplary collection device, showing microstructures (formed by etching or engraving a surface of a substrate into the shape of mesa, cavities, features, etc.) positioned within microfluidic channels, which are created by layering two or more substrates together within the collection device according to one embodiment of the invention.

FIG. 3D is a cross-sectional view of a microsized portion of the microfluidic chip device 300, cutting across the section "C" along the short portion (the width) of the microfluidic chip device 300. As shown in FIG. 3D, the dimension and height of the side-walls of the microstructures 114 and the cutout pattern and the thickness of the adhesive layer 304 may define the dimension, shape, and height of the plurality of the fluid channels 305 within the microfluidic chip device 300. As an example, the dimension of the plurality of the microstructures 114 may have a length of between about 50 mm and about 120 mm, a width of between about 1.5 mm and about 5.5 mm, and a height of about 30-120 µm.

As shown in FIGS. 3C-3D, the width and the direction of the carved out section (height) of the plurality of the microstructures 114 on the surface of the substrate 302 may be perpendicular to the flow direction and create a chaotic or disturbed flow of the blood, body fluid or biologic sample as it passes through the sealed channels within the microfluidic chip device 300. The disturbed flow enhances the contact between the surface coating and the biological substance of interest. Two factors determine the effectiveness of the microfluidic chip device in capturing the biological substance of interest. First, the flow rate of the blood, body fluid or biological sample may influence the contact time of the biological substance and the surface coating. A flow rate of about 0.1-1 ml/hr, such as about 0.5 ml/hr, is shown to ensure maximum binding of the biological substance to the surface coating. Second, the disturbance of the fluid flow created by the microstructures 114 on the solid surface 308 of the substrate 306 also affects capture efficiency. The disturbance increases contact time between the biological substance of interest and the surface coating.

In one embodiment, the collection device 110 with a large surface area is used to carry out a collection process and maximize the capturing sensitivity of a biologic substance of interest, without regard to imaging efficiency. For example, by increasing the surface area of the collection device by 4 times (e.g., increasing the numbers of microstructures 114 on its surfaces, the operation time for the collection device 110 is reduced by 75% while the total number of captured biologic substance of interest can be increased.

FIGS. 4A-4G illustrate various engraving patterns of the microstructures 114 that have been formed on the solid substrate and tested to determine the capture efficiency of collection devices 410A-410G. In FIG. 4A, the collection device 410A useful in the system 100 of FIGS. 1A-1C include a plurality of the microstructures 114 formed into a lined pattern. In FIG. 4B, the collection device 410B includes a plurality of the microstructures 114 formed into a pre-designed lined pattern, i.e., forming of the microstructure 114 in a group of two lines, which in turn are formed into a large group of one line. In FIG. 4D, the plurality of the microstructures 114 of the collection device 410D is a formed into groups of three lines and two lines, which in turn formed into yet another pre-designed lined pattern. In FIG. 4E, the plurality of the microstructures 114 of the collection devices 410E is formed into groups of three lines and two lines, which in turn formed into a horseshoe pattern. In FIG. 4F, the plurality of the microstructures 114 of the collection devices 410F is formed into groups of herringbone lines, which in turn formed into a lined herringbone patterned group and ultimately formed into a horseshow pattern. In FIG. 4G, the collection device 410G includes a plurality of the microstructures formed into groups of pre-arranged lines, which in turn formed into a pattern of 4 lines.

The capture efficiency of the collections devices 410A-410G is tested for different cancer cell lines spiked in serum or blood sample. Capture rate is defined as the percentage of the captured biological substance of interest versus the original biological substance in the testing sample. The collections devices 410G has the best arrangement of the pattern of the microstructures 114, achieving the highest biological substance capture rate.

FIGS. 6A-6H show examples of the concentration device 120 useful in the system 100 of FIGS. 1A-1C for concentrating a biologic substance of interest. The concentration device 120 of the system 100 may include a plurality of the microfeatures 124 arranged in one or more patterns positioned on one or more surfaces of concentration device 120 and configured to concentrate the biologic substance of interest 518 received by the concentration device 120 from the collection device 110.

Figure 6A:
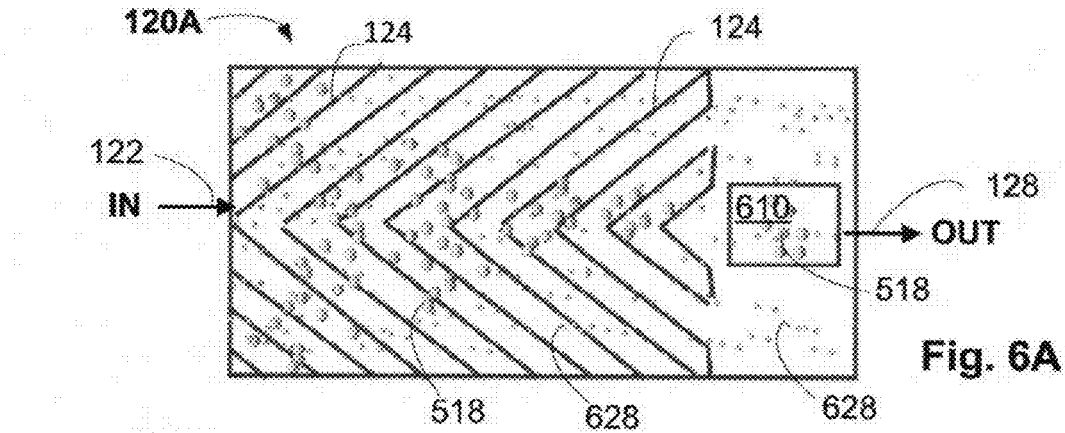
FIG. 6A is a top view of an exemplary concentration device useful in a system of FIGS. 1A-1C for concentrating a biologic substance of interest according to one embodiment of the invention.
Figure 6B:
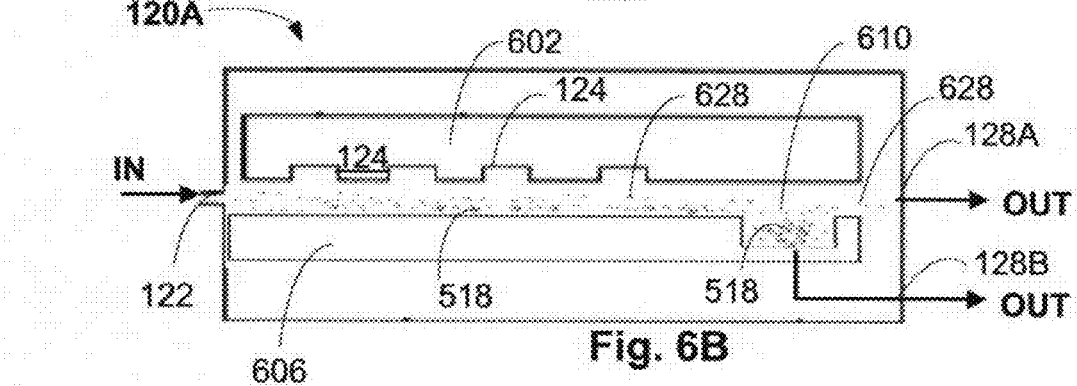
FIG. 6B is a cross-sectional view of a portion of the exemplary concentration device of FIG. 6A, showing the side-walls of micro-features within the concentration device according to another embodiment of the invention.

FIG. 6A is a top view of one example of a concentration device 120A. FIG. 6B is a cross-sectional view of a portion of the concentration device 120A of FIG. 6A, showing side-walls of the micro-features 124. Fluids, samples, buffers, and solutions can be delivered from the inlet 122 through the sample outlet 128 in a main fluid flow. The direction of the main fluid flow is sandwiched between a top substrate 602 and a bottoms substrate 606 within the concentration device 120 according to another embodiment of the invention.

The plurality of microfeatures 124 within the concentration device 120 may include trenches, vias, holes, cavities, mesa, grooves, slanted grooves, and other features which may be in microsizes or other sizes, etc., and be arranged in a pattern including, but no limited to, one or more lines, a horseshoe pattern, a herringbone pattern, one or more herringbone patterned lines, one or more lines of clustered microfeatures, and various combinations thereof, among others.

Not wishing to be bound by theory, it is contemplated that a pattern of the microfeatures 124 provide directed fluid flow paths within the concentration device, where cells, proteins and other components from the biologic sample are carried and delivered though the channels of the microfeatures 124 under hydrodynamic forces. In one example, a herringbone pattern of the microfeatures 124 may help drive the movement of the biologic substance of interest 518 toward the tip of the herringbones within the concentration device 120A, thereby concentrating a biologic substance of interest in the centralized herringbone tip area. In addition, because of the differences in sizes and weights for the biologic substance of interest 518 and the unwanted components 628, the use of hydrodynamic forces to drive the fluid flow and net driving forces within the plurality of the microfeatures 124 in carrying the biologic substance of interest 518 to a targeted area or location (e.g., a target concentration region 610) would reach an equilibrium and immobilize its carrying target (e.g., the biologic substance of interest 518), thereby concentrating and collecting the biologic substance of interest 518 in one subdivision or one area within the concentration device 120A.

The pattern of the microfeatures 124 can be used to direct one or more flows of the biologic substance of interest 518. Unwanted components 628, from the biologic sample or wash buffers, may be flown and carried by one or more fluid flows to flow out of the concentration device 120A via the sample outlet 128, thereby creating different flow paths for the biologic substance of interest 518 and the unwanted components 628.

In one embodiment, the plurality of microfeatures 124 may help to deliver the biologic substance of interest 518 to a target concentration region 610 and confine the biologic substance of interest 518 therein. The biologic substance of interest 518 accumulated and retained on the surface of the target concentration region 610 can later be retrieved (e.g., using a pipet or other means) and/or carried out of the concentration device 120. The target concentration region 610 may be formed near the sample outlet 128 and adapted to collect the biologic substance of interest 518. In one aspect, the target-concentration region 610 is a well having a surface area of between about 1 mm$^2$ and about 100 mm$^2$ (e.g., between about 1 mm$^2$ and about 16 mm$^2$, or between about 1 mm$^2$ and about 20 mm$^2$). The depth of the target-concentration region 610 can vary, such as between a few micron up to the thickness of the bottom substrate 606.

As the microfeatures 124 directs the flow of the biologic substance of interest 518 towards midline, the concentration of the biologic substance of interest 518 is highest around the centralized area near target concentration region 610. A concentration process using the concentration device 120 for a biologic substance of interest may include aligning of the biologic substance of interest using the microfeatures 124 disposed on a surface (e.g., a bottom surface of a top portion of the concentration device), and entrapping or concentrating the biologic substance of interest.

Figure 6C:
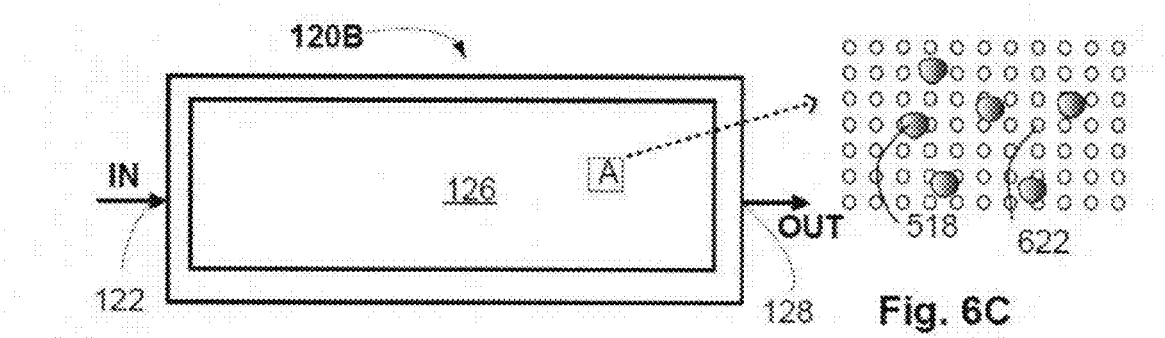
FIG. 6C is a top view of another exemplary concentration device useful in a system of FIGS. 1A-1C according another embodiment of the invention.
Figure 6D:
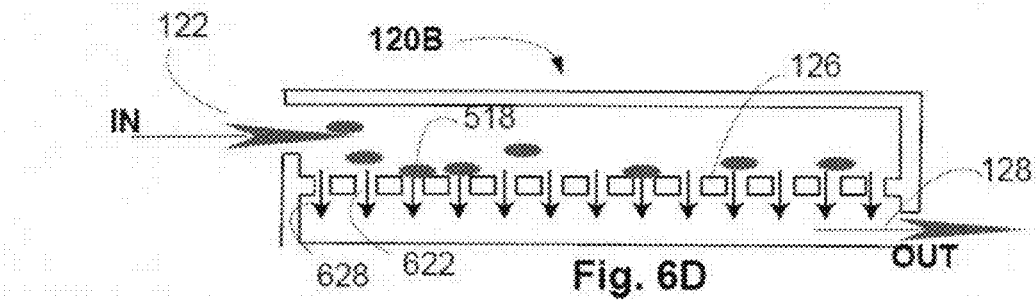
FIG. 6D is a cross-sectional view of a portion of the exemplary concentration device of FIG. 6C, showing the movement of the biologic substance of interest through an exemplary filter membrane within the concentration device according to one embodiment of the invention.

FIG. 6C shows another example of a concentration device 1208 useful in a system of FIGS. 1A-1C according another embodiment of the invention. FIG. 6D is a cross-sectional view of a portion of the concentration device 1208 of FIG. 6C. The concentration device 120B may include one or more filtration elements 126 (such as a filer membrane), positioned anywhere near the concentration device 120B, such as near the flow path of the biologic substance of interest 518.

In general, one or more filtration elements 126 can be placed horizontally and/or perpendicularly within a concentration device. The movement of the biologic substance of interest 518 may be directed from top surface of the filtration element 126 to the bottom surface of the filtration element 126, and/or from the top surface of the concentration device 120 to the bottom surface of the concentration device 120. In one embodiment, the filtration element 126 may be disposed adjacent to the target concentration region 610 of the concentration device 120A.

As shown in FIG. 6C, the filtration element 126 may include membrane pores 622 or through-holes where the size of the membrane pores 622 can be used to retain the biologic substance of interest 518 (as long as the size of the membrane pore 622, the cut-off size, is chosen to be smaller than the size of the biologic substance of interest 518), leaving the unwanted components 628 from a sample or a fluid flow to pass through the membrane pores 622, thereby concentrating the biologic substance of interest 518 on the surface of the filtration element 126. As an example, the filtration element 126 may contain a number of membrane pores 622 at a size of about 2 microns to about 8 microns in diameter to act as a filter. The filtration element may be positioned horizontally or vertically. As shown in FIG. 6D, the fluid flow from the inlet 122 is in a path parallel to the fluid flow leaving the sample outlet 128, thereby helping the removal of the unwanted components 628 from a sample or a fluid flow and concentrating the biologic substance of interest 518 on the surface of the filtration element 126. The filtration element 126 may be made from a material, including polyethylene (PE), polycarbonate (PC), polystyrene (PS), polymethyl methacrylate (pMMA), cyclic olefin copolymer (COC), polyvinylidene fluoride (PVDF), polyethersulfone (PES), cellulose esters, PTFE, nylon, polypropylene (PP), polyvinyl chloride (PVC), silicon, and glass, among others.

The filtration element 126 of the concentration device may be sandwiched between PDMS and PMMA substrates to form two adjacent chambers, separated by the filtration element 126. The top PMMA substrate may have an inlet to introduce a fluid sample into the upper chamber whereas the bottom PMMA substrate has an outlet to release the filtered fluid sample from the bottom chamber. The PDMS substrates are flexible enough to seal the two chambers to prevent fluid leakage, thereby making it substantially free of electrical elements or detachable mechanical parts, lowering the manufacturing cost, and minimizing electrochemical reactions which could adversely affect the viability of the obtained CTC target cells.

Not wishing to be bound by theory, it is contemplated that one or more of the following mechanisms are employed to align and entrap the biologic substance of interest: size-based filtration (see, Tan S J et ai., "Versatile label free biochip for the detection of circulating tumor cells from peripheral blood in cancer patients, Biosensors and Bioelectronics. 2010, 1701-1705, which is incorporated by reference in its entirety), dielectrophoresis (see, Hsiung L C et al., "A planar interdigitated ring electrode array via dielectrophoresis for uniform patterning of cells" Biosensors and Bioelectronics. 2008, 869-875, which is incorporated by reference in its entirety), fluid dynamics (such as inertia focusing; see Bhagat AAS et al., "Continuous particle separation in spiral microchannels using Dean flows and differential migration", Lab on a Chip. 2008; 8(11): 1906-14, which is incorporated by reference in its entirety, and herringbone structure), sedimentation and the like. One example of the fluid dynamic concentration process using hydrodynamic forces is illustrated in the concentration device 120A as shown in FIG. 6A-6B, and the size-based filtration process is illustrated in the concentration device 120B as shown in FIG. 6C-6D.

Figure 6E:
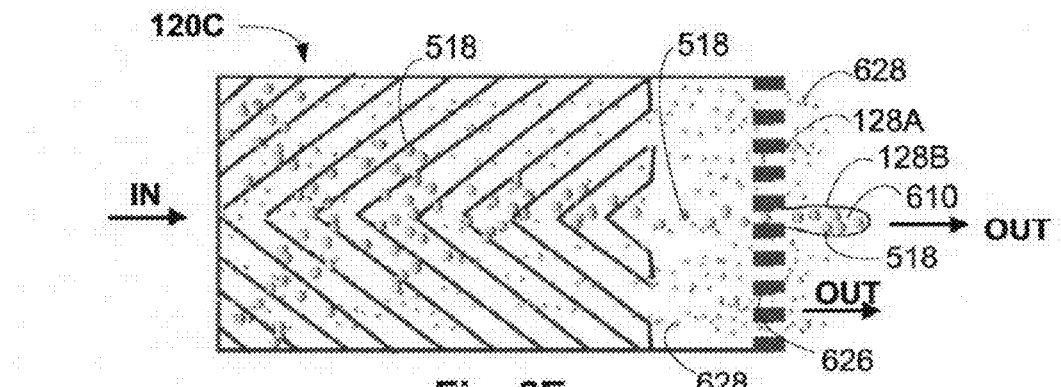
FIG. 6E is a top view of an exemplary concentration device useful in a system of FIGS. 1A-1C and illustrates the movement of the biologic substance of interest through a plurality of micro-features within the concentration device, thereby concentrating a biologic substance of interest to a subdivision of its outlet, according to one embodiment of the invention.
Figure 6F:
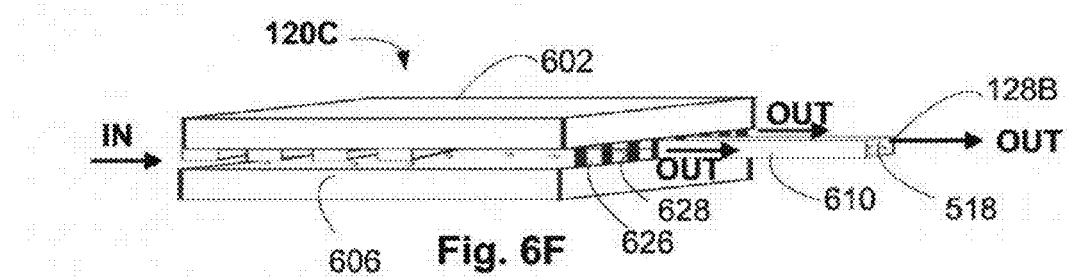
FIG. 6F is a perspective side view of a portion of the exemplary concentration device of FIG. 6E, showing the micro-features and channels within the concentration device and a subdivision of its outlet according to another embodiment of the invention.

FIG. 6E is a top view of a concentration device 120C useful in the system 100 of FIGS. 1A-1C. The concentration device 120C may include one or more channels 626 spatially arranged near the sample outlet 128. The channels 626 are provided to retain and help concentrate the biologic substance of interest 518 near a centralized area. FIG. 6F is a perspective side view of a portion of the concentration device 120C, showing the side-walls of the micro-features 124 and the channels 626. By being retained and collected in a centralizing area, the biologic substance of interest 518 can be easily recovered for further analysis. Unwanted components 628 can be discarded and removed from the concentration device 120C via channels 626.

Another embodiment of the invention provides the integration of one or more membrane-filtration elements with at least one or a combination of a plurality of microfeatures, a target-concentration region, one or more channels within the concentration device of the system. In one aspect, at least one filtration element is spatially arranged near the sample outlet 128. In another aspect, at least one filtration element 126 includes a filter membrane sandwiched between two adjacent chambers surrounded by one or more chamber walls being made of a material selected from the group consisting of polydimethyl-siloxane (PDMS), polymethyl methacrylate (PMMA), polyethylene (PE), polycarbonate (PC), polystyrene (PS), cyclic olefin copolymer (COC), silicon, glass, thermoplastics materials, and combinations thereof.

Figure 6G:
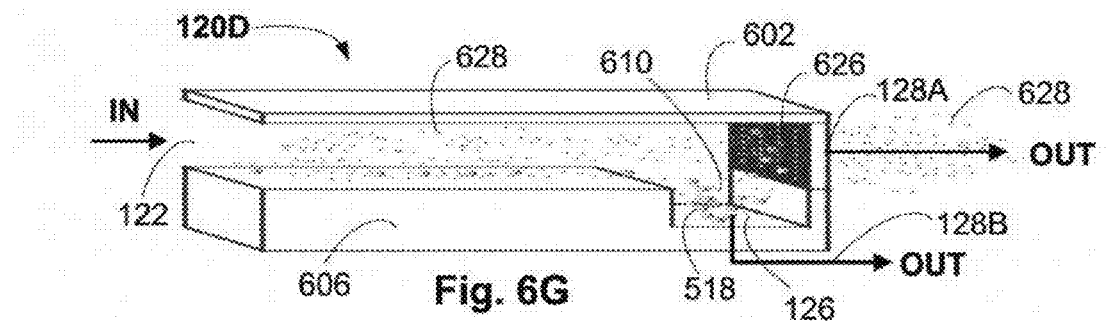
FIG. 6G is a perspective side view of another exemplary concentration device useful in a system of FIGS. 1A-1C, and illustrates the movement of the biologic substance of interest through the inner space within the concentration device, thereby concentrating a biologic substance of interest according to one embodiment of the invention.

FIG. 6G is a perspective side view of a concentration device 120C useful in the system 100 of FIGS. 1A-1C. In FIG. 6G, the movement of the biologic substance of interest through the inner space within the concentration device is shown, and the biologic substance of interest 518 is concentrated and retained in the target concentration area 610. Unwanted components 628 are flown and discarded out of the concentration device 120D by passing though one or more filtration membrane 126.

Figure 6H:
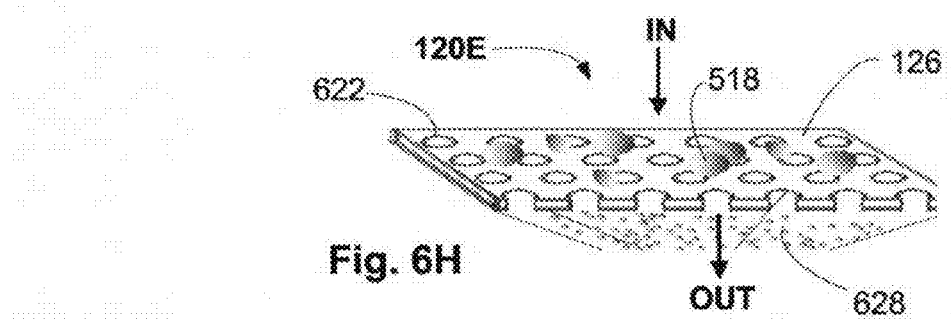
FIG. 6H is a perspective view of a portion of another exemplary concentration device useful in a system of FIGS. 1A-1C and illustrates the movement of the biologic substance of interest through an exemplary filter membrane within the concentration device for concentrating a biologic substance of interest according to one embodiment of the invention.

FIG. 6H shows another example and is a perspective view of a portion of a concentration device 120E useful in the system 100 of FIGS. 1A-1C. In FIG. 6H, fluids received from the collection device 110 comes in and passes thorough the membrane pores 622 of the filtration element 126 such that the biologic substance of interest 518 is able to retained on the surface of the filtration element 126., thereby concentrating the biologic substance of interest 518 thereon.

The collection and concentration devices of the system 100 of the present invention can capture, release, collect and concentrate the biologic substance of interest at a very small surface (such as the surface of the target concentration region 610 or the surface of the filtration element 126). This improves the efficiency of post-concentration analysis as only about 10 to about 100 magnified images are required for the small surface compared to several thousands of images required for the commercially available microfluidic chips. In addition, theses small surfaces where the biologic substance of interest are concentrated and captured on are mostly flat surfaces. Such flat surface design eliminates the need of z-dimensional scanning, improves the ability to identify focus plane without special algorithm and minimizes blurry images. As a result, the time for imaging the results of the captured, concentrated and/or obtained biologic substance for further analysis is effectively reduced from several hours (what are normally required for other types of commercially available microfluidic chips) to only minutes (e.g., about 1 to 20 minutes or less).

The biologic substance of interest are concentrated and entrapped in the target concentration region 610 of the concentration device by gravity and hence, fixation and centrifugation (which can affect cell viability) are avoided for subsequent immunostaining, inspection, characterization, molecular analysis, and/or other assays and analysis. Accordingly, by using the system 100 having the collection device 110 and the concentration device 120 as described herein, high yield (e.g., high concentration or high cell numbers) and high purity, and consistent system efficiency with high sensitivity ad and high specificity in capturing, collecting and concentrating a biologic substance of interest can be obtained from a biologic sample using the system and method described herein.

EXAMPLES

The following examples further illustrate the present invention. These examples are intended merely to be illustrative of the present invention and are not to be construed as being limiting.

Example 1

Preparation of the Two-Layer Surface Coating

Preparation of the nonfouling composition: Supported lipid bilayer (SLB) was prepared by dissolving POPC and b-PE (commercially available from Avanti Polar Lipids, USA) in chloroform, in a clean glass tube at a final lipid concentration of 5 mg/mL. The POPC/b-PE solution was dried by vortexing under a slow stream of nitrogen to form a thin, uniform POPC/b-PE film. The POPC/b-PE film was dried in a vacuum chamber overnight to remove residual chloroform. The dried POPC/biotin-PE film was dispersed in and mixed with a phosphate buffer containing 10 mM of phosphate buffered saline, 150 mM of sodium chloride aqueous solution, and 0.02% (w/v) of sodium azide (NaN3, commercially available from Sigma-Aldrich, USA), with the pH adjusted to 7.2. The mixed solution was filtered through 100-nm, followed by 50-nm Nuclepore® track-etched polycarbonate membranes (Whatman Schleicher & Schuell, Germany) for at least 10 times under 150 psi at room temp. The filtered solution was passed through LIPEX™ Extruder (Northern Lipids, Inc. Canada) to generate a homogenous population of unilamellar vesicles. The size of the POPC/biotin-PE vesicles was about 65±3 nm, determined by dynamic laser light scattering (Zetasizer Nano ZS, Malvern Instruments, Germany).

Polyelectrolyte multilayer (PEM) films was prepared by dissolving PLGA (MW=3000-15000) (Sigma, USA) or PLL (MW=15000-30000) (Sigma, USA) in a 10 mM Tris-HCl buffer (pH 7.4) with 150 mM NaCl. The concentrations of polypeptides were 1 mg/mL. The tPLL was immersed in 1 mL of PLGA counterionic solutions for 10 min at room temp to form t-(PLL/PLGA)1. After the coupling reaction, the samples were washed with pH 7.4 Tris-HCl buffer to remove any un-coupled polypeptides. Followed by the same coupling/wash cycle, a series of t-(PLL/PLGA)i (i=1 to 7.5) films were prepared, where i=1 referred to t-(PLL/PLGA)1, i=1.5 was referred to t-(PLL/PLGA)1-PLL, and so on.

Preparation of the Bioactive Composition.

Biotinylated EpCAM Antibody was prepared using an anti-EpCAM monoclonal antibody (OC98-1 or EpAb4-1) generated by method described by Chen et al (Clin Vaccine Immunol 2007; 14:404-11). The antibody was dissolved in a buffer solution containing 10 mM of PBS and 150 mM of NaCl, with a pH about 7.2. The concentration of the antibody buffer solution was about 0.65 mg/mL, determined by Nanodrop 1000 spectrophotometer (Thermo Scientific, USA). The antibody buffer solution was mixed with 10 mM of Sulfo NHS-LC-Biotin (with molar ratio of 1 to 10) and dissolved in Milli-Q water (Milli-Q RO system, USA) at room temperature for 30 min. Excess biotin was removed by dialysis in phosphate buffered saline at 4° C. for 24 h, with a buffer change every 12 h. Biotinylated antibody (bOC98-1 or bEpAb4-1) with a ratio of 1.5 moles of biotin to 1 mole of antibody was determined by the HABA assay using biotin quantitation kit (Pierce, USA). Alternatively, biotinylated goat anti-human anti-EpCAM antibody could be obtained from R and D Systems (Minneapolis, Minn.).

Preparation of Solid Substrate.

Glass microscope coverslips (commercially available from Deckglaser, Germany) were cleaned with 10% DECON 90 (Decon Laboratories Limited, England), rinsed with Milli-Q water, dried under nitrogen gas, and exposed to oxygen plasma in a plasma cleaner (Harrick Plasma, Ithaca, N.Y., U.S.A.) at 100 mtorr for 10 min. The glass substrate were used immediately after being rinsed with ethanol and dried under a stream of nitrogen gas.

Silicon oxide based solid substrates (e.g., silicon wafer or glass coverslips) were cleaned with piranha solution (70% sulfuric acid and 30% hydrogen peroxide (v/v)) at 120° C. for 40 min, washed with distilled water and rinsed with acetone. Solid substrates were dried under a stream of nitrogen and treated with a plasma cleaner. For the vapor phase silanization reaction, clean silicon oxide substrates and a Petri-dish containing 150 uL of 3-(aminopropyl)-triethoxysilane (Sigma, USA) were placed in a desiccator (Wheaton dry-seal desiccator, 100 nm) under reduced pressure at ~0.3 Torr for 16 h. The substrates were cleaned by acetone and dried with nitrogen stream.

Construction of the SLB Surface Coating on a Solid Substrate.

0.25 mg/ml of POPC/b-PE vesicle mixture from paragraph [0078] was added to the cleaned solid substrate to form a supported lipid bilayer (SLB), followed by an extensive rinse with a phosphate buffer containing 10 mM PBS and 150 mM NaCl (pH=7.2) to remove excess POPC/b-PE vesicles. 0.1 mg/mL of streptavidin (SA) solution (commercially available from Pierce Biotechnology, Rockford, Ill., USA) was added to the SLB coated solid substrate and incubated for 1 hour, followed by a rinse with PBS buffer to remove excess SA solution. About 0.05 mg/mL of b-Anti-EpCAM solution was added to the SA-SLB coated solid substrate to form the surface coating of the present invention.

Construction of the PEG Surface Coating on a Solid Substrate.

The biotinylated PEG silane solution (Si-bPEGs) was added to the clean substrate and incubated for 1 hour to form a Si-bPEG nonfouling composition on the solid substrate, followed by an ethanol rinse to wash out excess Si-bPEGs. 0.1 mg/mL of SA solution was added to the Si-bPEGs coated solid substrate and incubated for 1 hour, followed by PBS buffer rinse to remove excess SA. 0.05 mg/mL of b-Anti-EpCAM solution was added and bound with SA-Si-bPEGs surface coating, followed by PBS buffer rinse to remove excess b-Anti-EpCAM.

QCM-D Characterization of the SLB Surface Coating.

The construction of the surface coating was monitored by quartz crystal microbalance with dissipation (QCM-D). The QCM-D response in FIG. 11 shows the construction of the surface coating on a SiO2-pretreated quartz crystal. First, 0.25 mg/mL of POPC/b-PE vesicle mixture (in phosphate buffer) was dispensed into the QCM chamber at point (I). The normalized frequency change F and dissipation shift D were 26.0±0.7 Hz and 0.19±0.03×$10^{-6}$ respectively, which are the characteristics of highly uniformed lipid bilayer. After two buffer washes (denoted as *), 0.1 mg/mL of Streptavidin (SA) solution was dispensed at point II. DSA binding was saturated at F=52.8±5.4 Hz and D=3.84±0.54×$10^{-6}$. At point (III), 0.025 mg/mL of OC98-1 antibody solution was dispensed into the QCM chamber and there was no frequency or dissipation change. This shows there was no interaction between the OC98-1 antibody and the SA-lipid bilayer surface. In contrast, adding biotinylated antibody solution (bOC98-1 or bEpAb4-1) at point (IV) resulted in frequency and dissipation change, with equilibrated shifts of F=39.4±6.8 Hz and D=1.63±0.28×$10^{-6}$. This demonstrates the binding of biotinylated antibody to SA-lipid bilayer surface.

The characteristics of the SLB nonfouling composition on the surface coating were examined using QCM D. Bovine serum albumin (BSA, commercially available from Sigma-Aldrich, USA) was added to the surface coating and there was a sudden change in frequency and dissipation, with equilibrated shifts of F=6.9 Hz and D=3.35×$10^{-6}$. This indicates an immediate BSA adsorption. A buffer rinse caused an increase in frequency and a decrease in dissipation, with saturated shifts of F=6.1 Hz and D=3.16×$10^{-6}$. This indicates the adsorbed BSA can be easily removed from the surface coating and very weak interaction of BSA with the SLB.

Example 2

Preparation of a Microfluidic Chip

The microfluidic chip can be prepared by using a commercial CO2 laser scriber (Helix 24, Epilog, USA) to engrave the microtrenches to form microstructures on the PMMA substrate. The microfluidic chip, nuts, PMMA substrate and glass slides were cleaned with MeOH, detergent and water, followed by 10 min sonication. The nuts and the solid substrates were dried by nitrogen gas and baked for 10 min at 60° C. The PMMA substrate was bonded with nuts by chloroform treatment. The PMMA substrate and the glass slide were joined together using an adhesive (e.g. 3M tape from 3M, USA). The assembled chip was scraped by a plastic tip to tighten the bonded components.

Example 3

CTCs Binding to the Surface Coating

A total of 8 Blood samples were used to determine the CTC capture efficiency of the surface coating in the microfluidic chip in Example 2. Each blood sample contained 2 ml of blood samples from stage IV colon cancer patients and the sample was introduced to the sealed channel of the microfluidic chip at 0.5 ml/hr, controlled by a syringe pump. Subsequently, the sealed channel in the microfluidic chip was rinsed with 0.5 ml of PBS buffer at the flow rate of 1 ml/h, followed by in situ immunostaining.

The surface coating before and after the buffer rinse are compared. Prior to the buffer rinse, the surface coating was covered with non-specific blood cells and four CTCs. After the buffer rinse, almost all of the non-specific blood cells were removed-(upper-right) but the four CTCs (lower right) remained on the surface coating. The number of CTCs captured per ml of blood for these 8 samples were 26, 34, 36, 39, 47, 67 79, and 99. 25% of the blood samples had 79 or higher CTC count and the median CTC count was 43 per ml. There was minimal binding of the non-specific blood cells after the buffer rinse. As a comparison, the CTC count for the FDA approved Veridex CellSearch is as follows: 25% of the samples had 3 or more CTCs per 7.5 ml of testing sample and the median CTC counts was 0. The results show the surface coating of the present invention is effective in capturing CTCs and reducing the non-specific cell binding.

Example 4

Comparison of Capture Efficiency and Nonfouling Property of Various Surface Conditions The capture efficiency of HCT116 cells (biological substance) and nonfouling property to non-specific blood cells (white blood cells or WBC) of six different surface conditions are compared. The results show that the surface coatings of the present invention (lipid/SA/b-anti-EpCAM and PEG (15 mM)/SA/b-anti-EpCAM) are more effective in capturing the biological substance and reducing the binding of the non-specific blood cells on the surface coating.

Example 5

Purification by Flow

The differentiated flow shear could selectively "flush" out the non-specific blood cells based on the affinity of these cells to the nonfouling composition, while the biological substance remains on the surface coating. In this study, the surface coating comprised a SLB, a linker composition and fibronectin as the bioactive composition. Cells from two cell lines (fibroblast 3T3 and colon cancer cell line HCT116) were incubated on the surface coating for 4 h. The surface coating was rinsed with a buffer solution, which has a shear stress of 3 dyne/cm$^2$.

The HCT 116 cells were flushed away from the surface coating within 5 min of the buffer rinse. The fibroblast 3T3 cells still remained on the surface after 30 min of buffer rinse, due to its specific binding affinity to fibronectin. The results show that a low shear stress of about 3 dyne/cm$^2$ is sufficient to purify the biological substance on the surface coating. The results on respective shear stress and flushing time for the HCT116 and NIH-3T3 cell populations (non-specific blood cells) are compared. $N/N_0$ is the percentage of the cells remains attached to the surface coating using various shear stresses. N is the final cell number and $N_0$ is the initial cell number.

Example 6

Release of CTCs from the Surface Coating

The captured CTCs on the surface coating in Example 3 were released by introducing air bubbles. The results show that CTCs were removed from the surface coating in 3 seconds using the air bubble method.

Example 7

Culture of Released Cancer Cells from the Surface Coating

The captured cancer cells were incubated with 5 mM of EDTA at 37° C. for 5 to 10 min and were released by flowing a culture medium into the sealed channel of the microfluidic chip. A total of about 18 released colo205 cells, together with a serum-containing culture medium and antibiotics (penicillin+streptomycin+gentamicin) were placed into a 48-well tissue cultured polystyrene plate for cultivation. The outcome of the released colo205 cell culture demonstrates the colo205 cells released from the surface coating retain their viability for subsequent cell culture at day 10 and day 14.

Example 8

Capture CTCs Through a CTC Filtration Device

Any membranes, tubes, capillaries, or channels can be coated with the surface coating. A filtration device can be used, where the filtration filter is coated with a surface coating. The filter could accommodate high volume blood flow and capture a biological substance for a diagnostic or therapeutic purpose. To access the patient's blood or body fluid, a catheter is inserted into the patient's vein or fistula and the patient's blood flew through the CTC filtration device, wherein the surface coating on the filters capture the CTCs. The filtered blood then flew back to the patient.

While the foregoing is directed to embodiments of the present invention, other and further embodiments of the invention may be devised without departing from the basic scope thereof, and the scope thereof is determined by the claims that follow.

What is claimed:

1. A microfluidic flow-through system for enriching circulating tumor cells (CTCs) from a biologic sample, the system comprising:
a flow-through capture device comprising: (a) a sample inlet at a proximal end of the flow-through capture device configured to receive the biologic sample at a first concentration, (b) a fluid channel fluidly coupled to the sample inlet, wherein the fluid channel comprises one or more surfaces comprising a plurality of microstructures substantially perpendicular to a direction of bulk fluid flow and a surface coating attached to a portion of the one or more surfaces, wherein the surface coating comprises (1) a nonfouling lipid-bilayer composition, and (2) an antibody that selectively binds CTCs present within the biologic sample, and (c) an outlet at a distal end of the flow-through capture device;
a three-way valve in fluid communication with the flow-through capture device, the three-way valve comprising (a) a valve inlet fluidly coupled to the outlet of the flow-through capture device, (b) a first valve outlet for diverting away unwanted materials, and (c) a second valve outlet, wherein the three-way valve further comprises a first state and a second state, wherein in the first state, the three-way valve allows fluid flow from the flow-through capture device through the first valve outlet but not the second valve outlet, and wherein in the second state, the three-way valve allows fluid flow from the flow-through capture device through the second valve outlet but not the first valve outlet;
a flow-through concentration device in fluid communication with the three-way valve, wherein the flow-through concentration device is configured to receive the CTCs at a second concentration higher than the first concentration and concentrate the CTCs to a third concentration higher than the second concentration, wherein the flow-through concentration device comprises (a) an inlet in fluid communication with the second valve outlet of the three-way valve, (b) a concentration fluid channel comprising microfeatures arranged in a pattern that directs the CTCs towards a narrow region within the channel without directing unwanted components towards the narrow region, (c) a single well at a distal portion of the flow-through concentration device and within the narrow region of the channel, wherein the single well is located underneath a fluid flow path that leads towards (d) a sample outlet, wherein the single well is configured to entrap the CTCs flowing within the narrow region of the channel it via gravity while fluid flows over the single well via the fluid flow path towards the sample outlet, wherein a passage leading to a base of the single well is substantially perpendicular to the fluid flow path, wherein the single well is positioned toward a midline of the concentration device and the base of the single well has a substantially flat surface with an area of between about 1 mm$^2$ and about 100 mm$^2$, and wherein the sample outlet is located at a distal end of the flow-through concentration device and is configured to allow removal of the unwanted components from the system.

2. The system of claim 1, wherein the plurality of microstructures of the fluid channel of the flow-through capture device is arranged in one or more patterns.

3. The system of claim 2, wherein the plurality of microstructures within the capture device is arranged in a pattern selected from the group consisting of one or more lines, a horseshoe pattern, a herringbone pattern, one or more herringbone patterned lines, one or more lines of clustered microstructures, and various combinations thereof.

4. The system of claim 1, wherein the pattern of the microfeatures is selected from the group consisting of one or more lines, a horseshoe pattern, a herringbone pattern, one or more herringbone patterned lines, one or more lines of clustered microfeatures, and various combinations thereof.

5. The system of claim 1, wherein the single well is located near the sample outlet.

6. The system of claim 1, wherein one or more surfaces of the concentration device comprise one or more filtration elements.

7. The system of claim 6, wherein at least one membrane-filtration element of the concentration device comprises a filtration membrane sandwiched between two adjacent chambers surrounded by one or more chamber walls being made of a material selected from the group consisting of polydimethyl-siloxane (PDMS), polymethyl methacrylate (PMMA), polyethylene (PE), polycarbonate (PC), polystyrene (PS), cyclic olefin copolymer (COC), silicon, glass, thermoplastics materials, and combinations thereof.

8. The system of claim 1, wherein the concentration device further comprises one or more channels spatially arranged near the sample outlet.

9. The system of claim 4, wherein the pattern of the microfeatures comprises one or more channels and the biologic substance of interest is carried and delivered through the channels.

10. The system of claim 4, wherein the CTCs are carried and delivered under hydrodynamic forces to the single well.

11. The system of claim 1, wherein the concentration device comprises a filtration element.

12. The system of claim 11, wherein the filtration element is a filter membrane.

13. The system of claim 11, wherein the filtration element is placed horizontally within the concentration device.

14. The system of claim 12, wherein the filtration element is placed perpendicularly within the concentration device.

15. The system of claim 12, wherein the filtration element is disposed adjacent to the single well.

16. The system of claim 1, wherein the base of the single well comprises a filtration element.

17. The system of claim 16, wherein the flow-through concentration device comprises a second sample outlet located below the base of the filtration element.

18. The system of claim 16, wherein the flow-through concentration device comprises a second filtration element located at the sample outlet.

19. The system of claim 18, wherein the filtration element and the second filtration element are positioned substantially perpendicular to one another.

20. The system of claim 1, wherein the pattern is a herringbone pattern, and wherein the microfeatures are located on a top substrate of the flow-through concentration device and wherein the single well is located on a bottom substrate of the flow-through concentration device.

21. The system of claim 1, wherein the concentration fluid channel comprises a substantially constant width from a proximal end to the distal end of the flow-through concentration device.

* * * * *